US012806330B2

(12) United States Patent
Morris, Jr. et al.

(10) Patent No.: US 12,806,330 B2
(45) Date of Patent: Nov. 24, 2026

(54) INFUSING PUMPING SYSTEM INCLUDING DISPOSABLE CASSETTE AND PUMP

(71) Applicant: Altra, Inc., Redmond, OR (US)

(72) Inventors: Matthew G. Morris, Jr., Redmond, OR (US); Marco A. Schilling, San Diego, CA (US)

(73) Assignee: Altra, Inc., Redmond, OR (US)

( * ) Notice: Subject to any disclaimer, the term of this patent is extended or adjusted under 35 U.S.C. 154(b) by 366 days.

(21) Appl. No.: 18/664,156

(22) Filed: May 14, 2024

(65) Prior Publication Data

US 2024/0299643 A1 Sep. 12, 2024

Related U.S. Application Data

(63) Continuation of application No. 16/972,271, filed as application No. PCT/US2019/036004 on Jun. 7, 2019, now Pat. No. 12,017,038.
(Continued)

(51) Int. Cl.
*A61M 5/142* (2006.01)
*A61M 5/14* (2006.01)
(Continued)

(52) U.S. Cl.
CPC .......... *A61M 5/142* (2013.01); *A61M 5/1408* (2013.01); *A61M 5/365* (2013.01);
(Continued)

(58) Field of Classification Search
CPC .... A61M 5/142; A61M 5/1408; A61M 5/365; A61M 39/22; A61M 2005/14506;
(Continued)

(56) References Cited

U.S. PATENT DOCUMENTS

| | | | |
|---|---|---|---|
| 3,479,928 | A | 11/1969 | Noirot et al. |
| 5,055,001 | A | 10/1991 | Natwick et al. |

(Continued)

OTHER PUBLICATIONS

Written Opinion of PCT/US2019/036004 dated Oct. 28, 2019 [PCT/ISA/237].

(Continued)

*Primary Examiner* — Jason E Flick
(74) *Attorney, Agent, or Firm* — Sughrue Mion, PLLC

(57) ABSTRACT

Described is a large volume parenteral (LVP) infusion device system including a cassette and a pump. The system can include means for sensing pressure in a pump having a symmetric or matched, parallel dual chamber pumping mechanism and an attached cassette. The system can include a cassette having dual pumping chambers and a distal fitment, the distal fitment having an outlet port configured for attachment to tubing for infusion administration and being disposed on a distal end of the cassette, the distal fitment further including opposing cutouts. The system can also an air in line sensor, the AIL sensor configured to bracket the distal fitment at the position of the cutout when the cassette is loaded on the pump. The cassette can be mechanically coupled to the pump. The cassette can include a user actionable flow stop. The system can be configured for cassette misload protection.

4 Claims, 26 Drawing Sheets

Related U.S. Application Data

(60) Provisional application No. 62/681,858, filed on Jun. 7, 2018, provisional application No. 62/681,881, filed on Jun. 7, 2018, provisional application No. 62/681,950, filed on Jun. 7, 2018.

(51) Int. Cl.

| | |
|---|---|
| ***A61M 5/145*** | (2006.01) |
| ***A61M 5/36*** | (2006.01) |
| ***A61M 39/22*** | (2006.01) |

(52) U.S. Cl.
CPC ... *A61M 39/22* (2013.01); *A61M 2005/14506* (2013.01); *A61M 2205/12* (2013.01); *A61M 2205/332* (2013.01); *A61M 2205/3375* (2013.01)

(58) Field of Classification Search
CPC ........ A61M 2205/12; A61M 2205/332; A61M 5/14224; A61M 5/1413; A61M 5/16827; A61M 5/145; A61M 5/14; A61M 5/14212; A61M 5/1407; A61M 5/36; A61M 2205/123; A61M 2205/128; A61M 2205/121; A61M 5/168; A61M 5/16804; F04B 9/02; F04B 43/0081; F04B 53/22; F04B 43/02; F04B 43/04; F04B 9/00; F04B 43/00; F04B 43/0009; F04B 53/00
See application file for complete search history.

(56) References Cited

U.S. PATENT DOCUMENTS

| | | | | |
|---|---|---|---|---|
| 5,718,569 | A * | 2/1998 | Holst | F04B 43/12 604/153 |
| 6,110,410 | A | 8/2000 | Owens et al. | |
| 9,714,650 | B2 | 7/2017 | Morris, Jr. | |
| 2007/0233003 | A1 | 10/2007 | Radgowski et al. | |
| 2014/0363313 | A1 * | 12/2014 | Morris, Jr. | F04B 43/0054 417/63 |
| 2018/0010594 | A1 * | 1/2018 | Morris, Jr. | A61M 5/14224 |

OTHER PUBLICATIONS

International Search Report of PCT/US2019/036004 dated Oct. 28, 2019 [PCT/ISA/210].

* cited by examiner

RELATED ART

RELATED ART

INFUSING PUMPING SYSTEM INCLUDING DISPOSABLE CASSETTE AND PUMP

CROSS REFERENCE TO RELATED APPLICATIONS

This application is a Rule 53(b) Continuation of U.S. application Ser. No. 16/972,271 filed Dec. 4, 2020, which is a National Stage of International Application No. PCT/US2019/036004, filed Jun. 7, 2019, claiming the benefit of priority under 35 U.S.C. § 119(e) of U.S. Ser. No. 62/681,950, filed Jun. 7, 2018, U.S. Ser. No. 62/681,881, filed Jun. 7, 2018, and U.S. Ser. No. 62/681,858, filed Jun. 7, 2018, the contents of each of which are incorporated herein by reference in their respective entireties.

BACKGROUND

The disclosure relates generally to fluid pumping technology; relates specifically to an improved intravenous (IV) infusion pumping device and an improved disposable cassette; and relates more specifically to an improved means for mechanically interfacing a disposable cassette and an infusion pumping mechanism, an improved means for sensing pressure in a disposable cassette, and an improved means for reliable air in line (AIL) detection.

Large volume parenteral (LVP) intravenous (IV) infusion pumps on the market today are products of an evolutionary process of iterative design, evolving from the vented glass bottle and roller clamp to controlled drip rate through electronic drip counters, controllers and finally large volume displacement pumps. Advances in the industry have been incremental system refinements at best, dealing mostly with improvements in motor control software with complex software motor drive algorithms. While increasingly sophisticated software control has driven steady improvements in rate accuracy, continuity and flow uniformity over the years, inherent weaknesses in the fundamental design approach remain. Weaknesses that drive technical design challenges associated with accommodating safety and rate accuracy requirements across wide ranges of infusion rates, fluid viscosities, variations in differential pressure, and a host of other use conditions. These performance issues not only compromise performance but are critical to patient safety.

Large volume parenteral (LVP) intravenous (IV) infusion pumps are required by the FDA through ISO 60601 to be able to detect occlusions in the administration set, both upstream and downstream of the instrument. Restrictions, caused by kinks or patients rolling over on IV tubing, have the potential to cause occlusions which can interrupt the infusion and endanger the patient. Occlusion detection is accomplished by measuring the pressure inside the IV tubing and triggering an alarm when a pressure threshold is reached. The technology associated with measuring process fluid pressures is centuries old and well established. It is important to mention the relationship between force and pressure. Pressure applied over a defined area equals force. When we measure pressure, we are really measuring a resultant force. The greater the pressure, the greater the force. The greater the area, the greater the force. The transducers and sensors referenced in this document measure force. In this context, constraints unique to the medical device industry significantly compromise the reliability and accuracy of pressure measurement systems in drug delivery instruments.

Pressure sensors on many devices are independent, isolated subsystems often not fully considered at the system level until late in the development process. Some early IV pumps used mechanical limitations of the pump, such as motor stall, to limit pressure in the system. If an occlusion occurred between the pump and patient, the pump would continue to run until it was incapable of pumping against the back pressure. Other early devices used simple preset switches which offered very little utility. In contrast, an expanding variety of applications and sophisticated infusion regimens require more accurate and reliable pressure monitoring. An example would include applications requiring very low flow rates. Some critical drugs are delivered at rates under 10 milliliters per hour. Alarm thresholds must accommodate inaccuracies and all tolerance conditions to reduce the frequency of false positive, nuisance alarms. As a result, these alarms are artificially high and can require hours to build sufficient pressure to trigger an alarm. Clever software algorithms are used to mitigate fundamental inaccuracies by using the rate of change of pressure instead of actual gauge pressures. This has only served to increase the frequency of false alarms due to unanticipated dynamic pressure changes that occur during normal operation. Reliable, rapid occlusion detection and a reduction in the frequency of false alarms begins with reliable, sensitive, stable and accurate pressure measurement.

Maintaining sterility of the fluid path precludes practical direct access to internal pressure in the IV tubing. The alternative of measuring the pressure inside a tube from outside the tube is problematic at best. Cassette based devices typically dedicate an area of contact on a membrane, which can make the cassette difficult to prime but provides a relatively large contact area for the pressure transducer. In addition, cassette-based systems using diaphragms cannot measure negative pressures. Peristaltic devices typically add a dedicated diaphragm to the disposable assembly or simply press the transducer directly against the outside diameter of the IV tubing or silicone pumping segment. The small area of contact makes this approach less accurate but easier to prime. In either case, pressure is measured through an elastomeric material, so the resultant force becomes the combination of the internal pressure and the spring rate of the elastomer. The elastomeric barrier becomes part of the overall system tolerance stack. The physical properties of the elastomer, both in dimensional tolerances and deflection characteristics, have a first order effect on accuracy. Taken in the extreme, if the IV tubing was made of steel for instance, any changes in internal pressure would be negligible if measured through an inflexible steel wall.

A secondary consideration is that elastomers introduce significant hysteresis, which affects accuracy when pressures change. Hysteresis can be described as internal friction. This friction behaves much like a sticky gauge causing measurements to read low as pressures rise and high as pressures drop.

Another requirement of the pressure measurement system is the ability to read negative pressures. Pressures need to be monitored during the entire pumping cycle and portions of the pumping cycle generate negative pressure. An example would be the inlet side of the pump has to pull a vacuum to draw fluid into the pumping chamber. To satisfy this requirement, the sensor must be preloaded against the tubing or membrane. Relaxation of the elastomer over time reduces the offset force. This reduction in force contributes to measurement errors.

Accordingly, because of an inability to be in direct contact with the fluid path, internal pressures must be measured using changes in force transmitted through elastomeric barriers resulting in dimensional tolerances, changes in material properties, and the variability of the instrument/disposable interface all contributing and having a first order effect on gauge pressure errors.

In addition, reliable AIL detection is required for all large volume parenteral infusions devices (LVP). See, e.g., Code of Federal Regulations FDA title 21 section 880.5725.

Reliable AIL detection has been a significant technical challenge in the design of LVP Devices. Evidence of that challenge is that AIL detection has historically led the Pareto Chart for the industry since infusion devices were first introduced. Within the past 10 years, over 2.5 million IV pumps were recalled due to AIL related accidents or incidents according to the FDA's Maude database for adverse events.

Ultrasonic transducer pairs are well known and are typically used to detect air in IV tubing. The IV tubing is inserted between an emitter and receiver transducer pair when the set is loaded into the instrument. The emitter directs ultrasonic energy through the fluid path and into a mated detector. If the path is filled with fluid and the tubing is in intimate contact with both transducers, transmitted energy is directly coupled and received by the detector, and the signal strength should be high. However, air in the fluid path reduces the transmission of energy and the gain of the detector drops. When the signal strength drops below a preset threshold, an alarm is triggered, and the infusion is halted.

There are several ways air can be introduced into the fluid path. These include, for example, that the IV line was not properly primed; that there are leaks in the system; that the supply bag empties during an infusion; that silicone components in the system are porous to air; and that air can come out of solution to form bubbles over time when subject to low pressures.

Reliable operation depends on the IV tubing maintaining intimate contact with the transducer pair. If contact is reduced or broken, the signal to the detector is attenuated in the same way that the introduction of air triggers an alarm. This generates a false alarm. Loss of contact between the tubing and AIL sensor occurs frequently and is the root cause for the high frequency of nuisance AIL alarms in the field.

Care must be taken to properly insert the IV tubing into the AIL sensor pair. This is not automatic and must be done manually. Proper installation during set loading can mitigate, but not prevent false AIL alarms. However, this is an unrealistic expectation given the nature of the work load of the hospital staff, the lack of proper in-service instruction, and a belief by the engineers that the end user values the need or understands the theory of operation. Another major issue is that IV line is subject to distal strain from the patient moving in bed. Even a small amount of tugging on the tubing, downstream of the instrument, will stretch and detach the tubing from the AIL sensor. One last issue is that the tubing is a thermoplastic and is subject to a viscoelastic property called creep or "cold flow." When a constant force is applied over time, thermoplastics will flow in a direction away from concentrated stress. This means that the surface contact stress between the tubing and sensor will naturally reduce over time, reducing the output of the sensor.

The tubing, when loaded, is under compression or "squeezed" when inserted into the sensor. Even if the tubing is not being pulled, it is reacting to being squeezed. As mentioned above, thermoplastic materials may appear solid at room temperatures but actually behave as a very, very viscous liquid (i.e., creep or cold flow). This type of property can be seen in glass windows in very old buildings. Gravity causes the glass to "flow", which generates the optical distortion seen when trying to look through it. Thermoplastics behave in a way similar to glass, but flow more quickly. The thermoplastic material wants to physically "run away" from stress. This is not just a dent in the tubing. The material actually migrates. When the tubing is pulled out of the sensor, even after just an hour or so, a deformation can be seen from the compression generated by contact with the sensor. The reduction of the tubing section and subsequent reduction in surface contact stress required to "couple" the tubing to the ultrasonic sensor pair reduces the gain or output of the detector. This is similar to creating a wave guide for the ultrasonic energy passing through the fluid. As the surface contact stress reduces, the wave guide becomes more restrictive, and less of the transmitted energy gets to the detector, much like high resistance decreases the current flow through an electric circuit.

Distal strain generated by a patient pulling on the tubing is a different issue that would produce a similar "decoupling," even if the tubing was not a thermoplastic. The reduction in cross section is the result of a property called Poison Ratio. All materials exhibit a measurable reduction in cross section when stretched, even steel.

To affect a more robust, user friendly, and less error prone system, the interface between the administration set and the transducer pair should preferably be automatic; may preferably be easy to load; may preferably isolate the interface from external loads; and may preferably manage the surface contact stress profile of the tubing in contact with the sensor.

A new infusion pump system and disposable cassette, which addresses performance issues and weaknesses of the infusion pumps and cassettes in use today, is described in U.S. patent application Ser. No. 14/105,622, filed Dec. 13, 2013 (now U.S. Pat. No. 9,714,650) (hereinafter "Patent Document 1"). Patent Document 1 is hereby incorporated by reference in its entirety.

Referring to FIGS. 5A and 5B of the present application, Patent Document 1 discloses a pumping system 100 having a symmetric or matched, parallel dual pumping mechanism 101 with an interface to an attachable disposable cassette 200. The pumping system 100 includes a camshaft 104 that is positioned within the chassis 105 longitudinal to the axis of flow through the disposable and drives a pair of parallel drive arms 106, which pivot on separate hinges in line with the camshaft 104. The drive arms 106 are shown disposed within chassis 105 in parallel to motor 103, with a bottom portion of each being in mechanical communication with the camshaft 104 and a top portion connected to or integrally formed with pumping fingers 107. The drive arms 106 are shown hingedly mounted to the chassis 105 and in mechanical communication with the camshaft 104 and may be 180 degrees out of phase with each other, such that one chamber of the disposable cassette pumps while the opposing chamber fills. The pumping mechanism 101 also includes a plurality of valve arms 102 in mechanical communication with the camshaft 104.

Referring to FIGS. 6A and 6B of the present application, the disposable cassette 200 described in Patent Document 1 includes dual pumping chambers 205, a membrane 203, an inlet port 201, an outlet port 202, and may include one or more convolutions 204 configured to allow the membrane 203 to follow the motion of the pumping finger with little or no resistance. The disposable cassette 200 includes an open bottom side 208 (which is sealed by the membrane 203), inlet valves 206 and outlet valves 207, wherein the valves are positioned to interface with a plurality of valve arms 102 of the pumping system 101.

Referring to FIGS. 7A-7C, Patent Document 1 discloses that the pumping system 100 may include an electronic strain gauge 121 to sense the pressure being applied by the fluid within each of the pumping chambers. Patent Document 1 discloses that a strain gauge 121 may be attached to the back side 120 (i.e., the side opposite to the attachment surface to the membrane 203) of each pump finger 107 of the drive arm 106.

Patent Document 1 discloses that, because the membrane 203 has zero spring rate and is supported against vacuum loads by attachment to the pumping finger 107 of the drive arm 106, the multi-laminate membrane 203 does not need to be preloaded by the disposable. Additionally, because the pressure is acting over the entire top surface of the pumping finger, hysteresis is minimized and gauge pressure accuracy is far superior to other systems constrained to work through a preloaded, elastomeric interface. As such, the force measured is truly the internal pressure of the fluid within the pumping chamber over the contact area of the pumping finger 107. However, the present inventors discovered that the means for sensing pressure disclosed by Patent Document 1 could be improved.

According to Patent Document 1, the membrane 203 of the disposable cassette 200 is configured to be held in contact with the pumping fingers 107 of the pumping mechanism 101 by electrostatic attraction or magnetic attraction, such as by an array of permanent magnets 108 disposed on the pumping fingers 107 of the drive arms 106, thereby allowing the pump 101 to pull a vacuum without the need for a preloaded elastomeric pumping segment. However, the present inventors discovered that the means disclosed by Patent Document 1 for electrostatically or magnetically interfacing and releasably coupling the cassette to the pump could be improved.

In addition, Patent Document 1 does not address AIL detection. Accordingly, objectives of the non-limiting embodiments described herein include addressing the issues described above to provide a more robust, user friendly, and less error prone system, and improving the infusion pump system disclosed in Patent Document 1.

SUMMARY

The non-limiting embodiments of the present disclosure are directed to an infusion pump system addressing the challenges of pressure measurement and reliable AIL detection discussed above. In addition, the non-limiting embodiments of the present disclosure are directed to improvements to both the pumping mechanism and the cassette of the new infusion pump system 100 disclosed by Patent Document 1.

In a non-limiting embodiment, an infusing pumping system is disclosed including (A) a disposable cassette including dual pumping chambers sealed by a membrane; and (B) a pumping mechanism, the pumping mechanism including a chassis configured for removable attachment to the disposable cassette; a motor disposed within the chassis; a camshaft in mechanical communication with the motor; a first drive arm hingedly attached to the chassis, wherein a bottom portion of the first drive arm is in mechanical communication with the camshaft at a first point of contact, and a top portion of the first drive arm is coupled to the disposable cassette at a portion of the membrane covering the first pumping chamber; a second drive arm hingedly attached to the chassis, wherein a bottom portion of the second drive arm is in mechanical communication with the camshaft at a second point of contact, and a top portion of the second drive arm is coupled to the disposable cassette at a portion of the membrane covering the second pumping chamber, and wherein the first and second drive arms are 180 degrees out of phase with each other during operation of the pumping mechanism; and a plurality of valve arms hingedly attached to the chassis, wherein a lower portion of each valve arm is in mechanical communication with the camshaft and an upper portion of each valve arm is configured to respectively actuate each of the first inlet valve, the second inlet valve, the first outlet valve, and the second outlet valve of the disposable cassette, wherein a first force sensor is attached to the bottom portion of the first drive arm. In this embodiment, the infusion pumping system can include an AIL senor; the pumping mechanism can have means for mechanically coupling to the disposable cassette; and the disposable cassette can have means for mechanically coupling to the pumping mechanism and means for facilitating reliable AIL detection.

In a non-limiting embodiment of the infusion pumping system, a second force sensor is attached to the bottom portion of the second drive arm.

In a non-limiting embodiment of the infusion pumping system, the first force sensor includes a strain gauge. In another non-limiting embodiment, the first force sensor and the second force of the infusion pumping system each include a strain gauge.

In a non-limiting embodiment of the infusion pumping system, the force sensor is attached to a cross section of the first drive arm that is not subject to torsional or off-center loads. In one embodiment of the infusion pumping system, the force sensor is attached to a rectangular cross section of the first drive arm.

In a non-limiting embodiment of the infusion pumping system, the first force sensor is positioned closer to the first point of contact than a point of contact of the top portion of the first drive arm with the disposable cassette In a non-limiting embodiment of the infusion pumping system, the pumping mechanism includes a compression spring, wherein the compression spring is positioned through the first point of contact.

In a non-limiting embodiment of the infusion pumping system, the pumping mechanism of the infusion pumping system includes a compression spring that acts directly against the first point of contact of the first drive arm with the cam. In another non-limiting embodiment, the pumping can also include a second compression spring that acts directly against the second point of contact of the first drive arm with the cam.

In another non-limiting embodiment, an infusing pumping system is disclosed which includes: (A) a disposable cassette having a shell including a first pumping chamber, and a second pumping chamber; a means for controlling fluid flow from the first pumping chamber; a means for controlling fluid flow from the second pumping chamber; and a means for sealing the first pumping chamber and the second pumping chamber; and (B) a means for pumping including: a means for actuating the first pumping chamber and the second pumping chamber 180 degrees out of phase with each other during operation of the means for pumping; a means for actuating the means for controlling fluid flow from the first pumping chamber; a means for actuating the means for controlling fluid flow from the second pumping chamber; and a means for sensing pressure in the first pumping chamber, wherein the means for sensing pressure in the first chamber is attached to a section of the means for pumping that is not subject to torsional or off-center loads.

In a non-limiting embodiment of the infusion pumping system, the infusion pumping system further includes a means for sensing pressure in the second pumping chamber, wherein the means for sensing pressure in the second chamber is attached to a section of the means for pumping that is not subject to torsional or off-center loads.

In another non-limiting embodiment, an infusing pump is disclosed which includes a chassis configured for removable attachment to a disposable cassette; a motor disposed within the chassis; a camshaft in mechanical communication with the motor; a first drive arm hingedly attached to the chassis, wherein a bottom portion of the first drive arm is in mechanical communication with the camshaft at a first point of contact, and a top portion of the first drive arm is configured for coupling to the disposable cassette; a second drive arm hingedly attached to the chassis, wherein a bottom portion of the second drive arm is in mechanical communication with the camshaft at a second point of contact, and a top portion of the second drive arm is configured for coupling to the disposable cassette, and wherein the first and second drive arms are 180 degrees out of phase with each other during operation of the pumping mechanism; and a plurality of valve arms hingedly attached to the chassis, wherein a lower portion of each valve arm is in mechanical communication with the camshaft and an upper portion of each valve arm is configured to actuate valves of the disposable cassette, wherein a first force sensor is attached to the bottom portion of the first drive arm.

In a non-limiting embodiment of the infusion pump, the infusion pump further includes a second force sensor attached to the bottom portion of the second drive arm.

In a non-limiting embodiment of the infusion pump, each of the first force sensor and the second force sensor includes a strain gauge.

In a non-limiting embodiment of the infusion pump, the first force sensor is attached to a cross section of the first drive arm that is not subject to torsional or off-center loads In a non-limiting embodiment of the infusion pump, the first force sensor is attached to a rectangular cross section of the first drive arm.

In a non-limiting embodiment of the infusion pump, the infusion pump further includes a first compression spring and a second compression spring, wherein the first compression spring acts directly against the first point of contact, and the second compression spring acts directly against the second point of contact.

In a non-limiting embodiment of the infusion pump, the top portion of the first drive arm is configured to mechanically couple to the disposable cassette, and the top portion of the second drive arm is configured to mechanically couple to the disposable cassette.

In another non-limiting embodiment, an infusing pumping system is disclosed, which includes: (A) a disposable cassette comprising: a shell having a sealed top side, an open bottom side, a proximal fitment having an inlet port at a proximal end thereof, and a distal fitment having an outlet port at a distal end thereof; a first inlet valve and a second inlet valve in communication with the inlet port; a first outlet valve and a second outlet valve in communication with the outlet port; a first pumping chamber disposed within the open bottom side of the shell and in communication with the first inlet valve and the first outlet valve; a second pumping chamber disposed within the open bottom side of the shell and in communication with the second inlet port and the second outlet port, the first pumping chamber and the second pumping chamber being positioned on opposing sides of a central axis of the shell extending from the inlet port to the outlet port; and a membrane sealing the open bottom side of the shell; and (B) a pump comprising: a chassis configured for removable attachment to the disposable cassette; a motor disposed within the chassis; a camshaft in mechanical communication with the motor; a first drive arm hingedly attached to the chassis, wherein a bottom portion of the first drive arm is in mechanical communication with the camshaft at a first point of contact, and a top portion of the first drive arm is coupled to the disposable cassette at a portion of the membrane covering the first pumping chamber; a second drive arm hingedly attached to the chassis, wherein a bottom portion of the second drive arm is in mechanical communication with the camshaft at a second point of contact, and a top portion of the second drive arm is coupled to the disposable cassette at a portion of the membrane covering the second pumping chamber, and wherein the first and second drive arms are 180 degrees out of phase with each other during operation of the pumping mechanism; and a plurality of valve arms hingedly attached to the chassis, wherein a lower portion of each valve arm is in mechanical communication with the camshaft and an upper portion of each valve arm is configured to respectively actuate each of the first inlet valve, the second inlet valve, the first outlet valve, and the second outlet valve of the disposable cassette. In this non-limiting embodiment, the distal fitment can be configured for attachment to tubing for infusion administration to a subject; the distal fitment of the disposable cassette can include opposing cutouts; the pump further can include an air in line sensor; and when the disposable cassette is attached to the chassis, the air in line sensor can bracket the distal fitment at the opposing cutouts.

In a non-limiting embodiment of the infusion pumping system, the air in line sensor includes an ultrasonic transducer pair.

In a non-limiting embodiment of the infusion pumping system, when the distal fitment is attached to the tubing, the tubing is bonded to a first portion of the distal fitment that is proximal to the opposing cutouts and is also bonded to a second portion of the distal fitment that is distal to the opposing cutouts.

In a non-limiting embodiment of the infusion pumping system, when the disposable cassette is attached to the chassis, the first portion of the distal fitment is at a position proximal to the air in line sensor, and the second portion of the distal fitment is at a position distal to the air in line sensor.

In a non-limiting embodiment of the infusion pumping system, when the disposable cassette is attached to the chassis, the outlet port of the disposable cassette is distal to the air in line sensor.

In a non-limiting embodiment of the infusion pumping system, the chassis includes a bezel having a shape corresponding to a cross sectional shape of the disposable cassette, which provides misload protection.

In a non-limiting embodiment of the infusion pumping system, the disposable cassette has a shape configured for attachment to the pump in a single way for misload protection.

In another non-limiting embodiment, a disposable cassette is disclosed for use with an infusion pumping system, the disposable cassette can include: a shell having a sealed top side, an open bottom side, a proximal fitment having an inlet port which is configured for fluid communication with an external fluid reservoir and which is disposed on a proximal end of the cassette, and a distal fitment having an outlet port which is configured for attachment to tubing for infusion administration to a subject and which is disposed on a distal end of the cassette; a first inlet valve and a second inlet valve, the first inlet valve and the second inlet valve being in discrete fluid communication with the inlet port; a first outlet valve and a second outlet valve, the first outlet valve and the second outlet valve being in discrete fluid communication with the outlet port; a first pumping chamber which is disposed within the open bottom side of the shell and which is in discrete fluid communication with the first inlet valve and the first outlet valve; a second pumping chamber which is disposed within the open bottom side of the body and which is in discrete fluid communication with the second inlet valve and the second outlet valve; and a membrane sealing the open bottom side of the body to define, in combination with the first and second pumping chambers, dual fluid paths between the inlet port and the outlet port. In this non-limiting embodiment, the first pumping chamber and the second pumping chamber can be positioned on opposing sides of a central axis of the shell extending from the inlet port to the outlet port, and the distal fitment can include opposing cutouts.

In a non-limiting embodiment of the disposable cassette, the disposable cassette includes a flow stop, the flow stop including a user actuator configured for opening and closing a flow of fluid to the distal fitment.

In a non-limiting embodiment of the disposable cassette, the first inlet valve, the second inlet valve, the first outlet valve, and the second outlet valve are configured to be independently actuated by an infusion pumping system.

In a non-limiting embodiment of the disposable cassette, the dual fluid paths include: a first fluid path including the inlet port, the outlet port, and the first pumping chamber; and a second fluid path including the inlet port, the outlet port, and the second pumping chamber, and wherein the first fluid path is parallel to the second fluid path with respect to the central axis extending from the inlet port to the outlet port.

In a non-limiting embodiment of the disposable cassette, the membrane is a single layer of a thermoplastic elastomer.

In a non-limiting embodiment of the disposable cassette, the first and second pumping chambers have equal volumes.

In a non-limiting embodiment of the disposable cassette, the disposable cassette has an asymmetric cross-sectional shape.

In a non-limiting embodiment, the disposable cassette further includes a means for mechanically coupling the disposable cassette to an infusion pumping system.

In a non-limiting embodiment, the disposable cassette further includes a pair of slots configured to mechanically couple to a pair of corresponding male interlocking features of an infusion pumping system.

In a non-limiting embodiment, the disposable cassette further includes a mechanical coupler configured to couple the disposable cassette to an infusion pumping system.

Another non-limiting embodiment of the present disclosure involves releasably coupling the disposable cassette to the drive elements of the pumping mechanism using a mechanical connection. A benefit of this non-limiting embodiment is the elimination of the conventional need to rely on the spring rate, fatigue and strength characteristics of compliant elastomers to prime the pumping chamber.

In another non-limiting embodiment, an infusing pumping system is disclosed including: (A) a disposable cassette comprising: a body having a sealed top side, an open bottom side, an inlet port, and an outlet port; a first inlet valve and a second inlet valve in communication with the inlet port; a first outlet valve and a second outlet valve in communication with the outlet port; a first pumping chamber disposed within the open bottom side of the body and in communication with the first inlet valve and the first outlet valve; a second pumping chamber disposed within the open bottom side of the body and in communication with the second inlet port and the second outlet port, the first pumping chamber and the second pumping chamber being positioned on opposing sides of a central axis of the body extending from the inlet port to the outlet port; and a membrane sealing the open bottom side of the body, the membrane comprising a first female feature associated with the first pumping chamber and a second female feature associate with the second pumping chamber; and (B) a pumping mechanism including: a chassis configured for removable attachment to the disposable cassette; a motor disposed within a length of the chassis and positioned in parallel to the central axis extending between the inlet port and the outlet port of the disposable cassette when the disposable cassette is attached to the pumping system; a camshaft in mechanical communication with the motor; a first drive arm hingedly attached to the chassis and positioned parallel to the motor, wherein a bottom portion of the first drive arm is in mechanical communication with the camshaft, and a top portion of the first drive arm has a first male feature configured for coupling to the first female feature of the disposable cassette; a second drive arm hingedly attached to the chassis and positioned parallel to the motor, wherein a bottom portion of the second drive arm is in mechanical communication with the camshaft, and a top portion of the second drive arm has a second male feature configured for coupling to the second female feature of the disposable cassette, and wherein the first and second drive arms are 180 degrees out of phase with each other during operation of the pumping mechanism; and a plurality of valve arms hingedly attached to the chassis, wherein a lower portion of each of the valve arms is in mechanical communication with the camshaft and an upper portion of each of the valve arms is configured to respectively actuate each of the first inlet valve, the second inlet valve, the first outlet valve, and the second outlet valve of the disposable cassette.

In a non-limiting embodiment of the infusion pumping system, a main surface of each drive arm of the pumping mechanism that is in contact with the membrane of the disposable cassette has means for mechanically coupling to the membrane of the disposable cassette.

In a non-limiting embodiment of the infusion pumping system, the means for mechanically coupling the drive arms to the cassette is located orthogonal to the contacting face of the cassette, centered on the axis of rotation of the drive arms, and longitudinal to the axis of flow of fluid through the disposable cassette.

In a non-limiting embodiment of the infusion pumping system, the means for mechanically coupling is a male interlocking feature.

In a non-limiting embodiment of the infusion pumping system, the male interlocking feature includes a blade, a rib or a vane positioned longitudinal to the axis of flow, orthogonal to the flat surface area of the drive arm contacting the disposable cassette, and centered on the axis of rotation.

In one a non-limiting embodiment of the infusion pumping system, the disposable cassette has means for mechanically coupling the male interlocking feature.

In a non-limiting embodiment of the infusion pumping system, the means for mechanically coupling to the male interlocking feature is a female feature on the disposable cassette.

In a non-limiting embodiment of the infusion pumping system, the female feature on the disposable cassette is a slot configured for releasably interfacing with the male interlocking feature.

In a non-limiting embodiment of the infusion pumping system, the cassette can include a flow stop, the flow stop including a user actuator configured for opening and closing a flow of fluid to the distal fitment.

In a non-limiting embodiment of the infusion pumping system, the flow stop can be configured to cover the first outlet valve and the second outlet valve when the flow stop is in a closed position.

In a non-limiting embodiment, an infusing pump includes a motor disposed within a length of a chassis and positioned in parallel to a flow path of fluid when a cassette is loaded on the infusion pump, and a means for actuating drive arms and valve arms.

In a non-limiting embodiment, the means for actuating drive arms and valve arms includes a camshaft (or cam) disposed adjacent to and in mechanical communication with the motor, wherein the camshaft include a plurality of lobes disposed along a length thereof.

In a non-limiting embodiment of the infusion pump, the plurality of lobes can include a main lobe configured to actuate each of the first and second drive arms, a first valve lobe configured to actuate the inlet valve arms, and a second valve lobe configured to actuate the outlet valve arms.

BRIEF DESCRIPTION OF THE DRAWINGS

Features, advantages and technical and industrial significance of exemplary embodiments of the present disclosure will be described below with reference to the accompanying drawings, in which like numerals denote like elements, and wherein.

DETAILED DESCRIPTION

Described herein are non-limiting embodiments an IV infusion pump mechanism and a disposable cassette that is fundamentally different from conventional systems; non-limiting embodiments that address the pressure measurement and AIL detection challenges discussed above; and non-limiting embodiments that improve upon the new infusion pump system 100 disclosed by Patent Document 1.

Managing tolerances and compliance requires a fundamental change in the approach to intravenous ("IV") fluid delivery system design. Performance related issues fall into four general categories: (1) system compliance, (2) component tolerance sensitivity, (3) serial nature of the pumping systems, and (4) the dimensional stability of the disposable/instrument interface. Foremost is the reliance of the strength and stability of elastomeric membranes and tubing segments to pull fluid into the pumping chamber.

As noted above, non-limiting embodiments of the interface between the pumping mechanism and disposable cassette disclosed herein involve releasably coupling the disposable cassette to the drive elements of the pumping mechanism mechanically. A benefit of these non-limiting embodiments is the elimination of the conventional need to rely on the spring rate, fatigue and strength characteristics of compliant elastomers to prime the pumping chamber. Another benefit is that it provides a system with the ability to achieve highly accurate and reliable pressure measurement.

To highlight the potential of the non-limiting embodiments described herein, a detailed description of how these four issues are addressed, in the context of two of the most clinically important performance criteria, is described below.

It is a requirement that fluid delivery systems be self-priming. That is, the pump mechanism needs to be able to draw fluid into the pump even if the supply container is below the level of the instrument. The mechanism drive arms of the system described here, unlike competitive instruments that typically use sliding fingers, pivot around centers just outboard of the two pumping chambers. This is shown, for example, in FIGS. 5A, 5B, 6A and 6B (which are reproduced from Patent Document 1). This is also shown in FIGS. 1A, 3A and 4C, wherein FIG. 1A shows a side view of a pumping system of the type disclosed in Patent Document 1, wherein the system shown in FIG. 1A also includes, for example, a non-limiting embodiment of the mechanical coupling means disclosed herein.

Figure 3A:
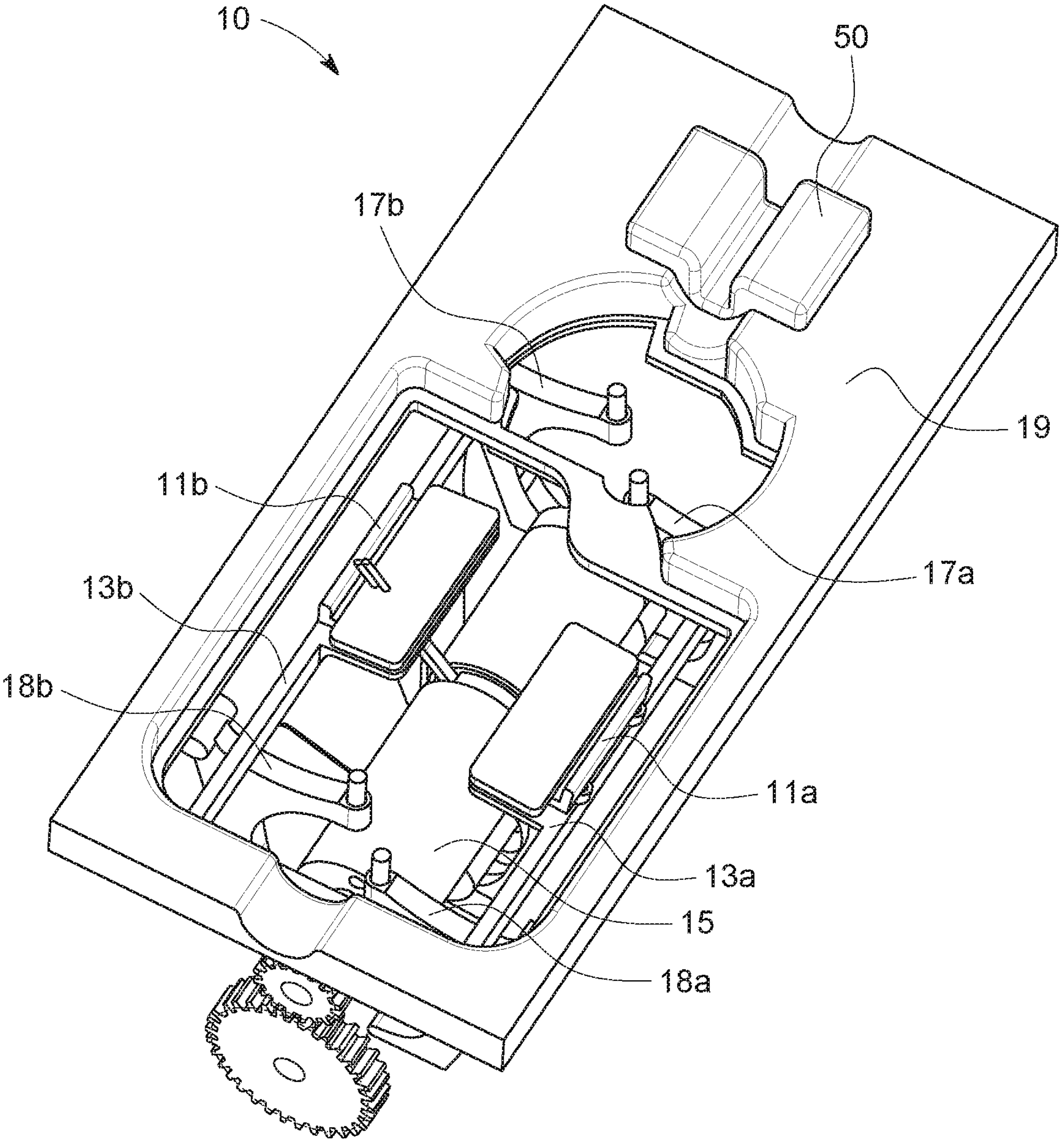
FIG. 3A shows a perspective view of a pumping mechanism according to a non-limiting embodiment of the disclosure.

In addition, FIG. 3A shows a perspective view of a non-limiting embodiment of a pumping mechanism 10 of the type disclosed in Patent Document 1. For example, FIG. 3A shows the chassis (unlabeled), case bezel 19, motor 15, drive arms 13 (specifically, first and second drive arms 13*a*, 13*b*) which, first and second outlet valve arms 17*a*, 17*b*, and first and second inlet valve arms 18*a*, 18*b*. The motor 15 is shown disposed within a length of the chassis and positioned in parallel to the flow path of fluid when a cassette is loaded on the pumping mechanism 10, and a cam (or camshaft) (unlabeled in FIG. 3A) can be disposed adjacent to and in mechanical communication with the motor 15, wherein the camshaft can include a plurality of lobes disposed along a length thereof (e.g., the plurality of lobes can include a main lobe configured to actuate each of the first and second drive arms 13*a*, 13*b*, a first valve lobe configured to actuate the inlet valve arms 18*a*, 18*b* and a second valve lobe configured to actuate the outlet valve arms 17*a*, 17*b*). A general discussion of the operation of these elements of the pumping mechanism 10 is described in Patent Document 1, which is incorporated by reference in its entirety. FIG. 3A also shows an AIL sensor 50, discussed in more detail below.

Mechanical Coupling

Figure 1A:
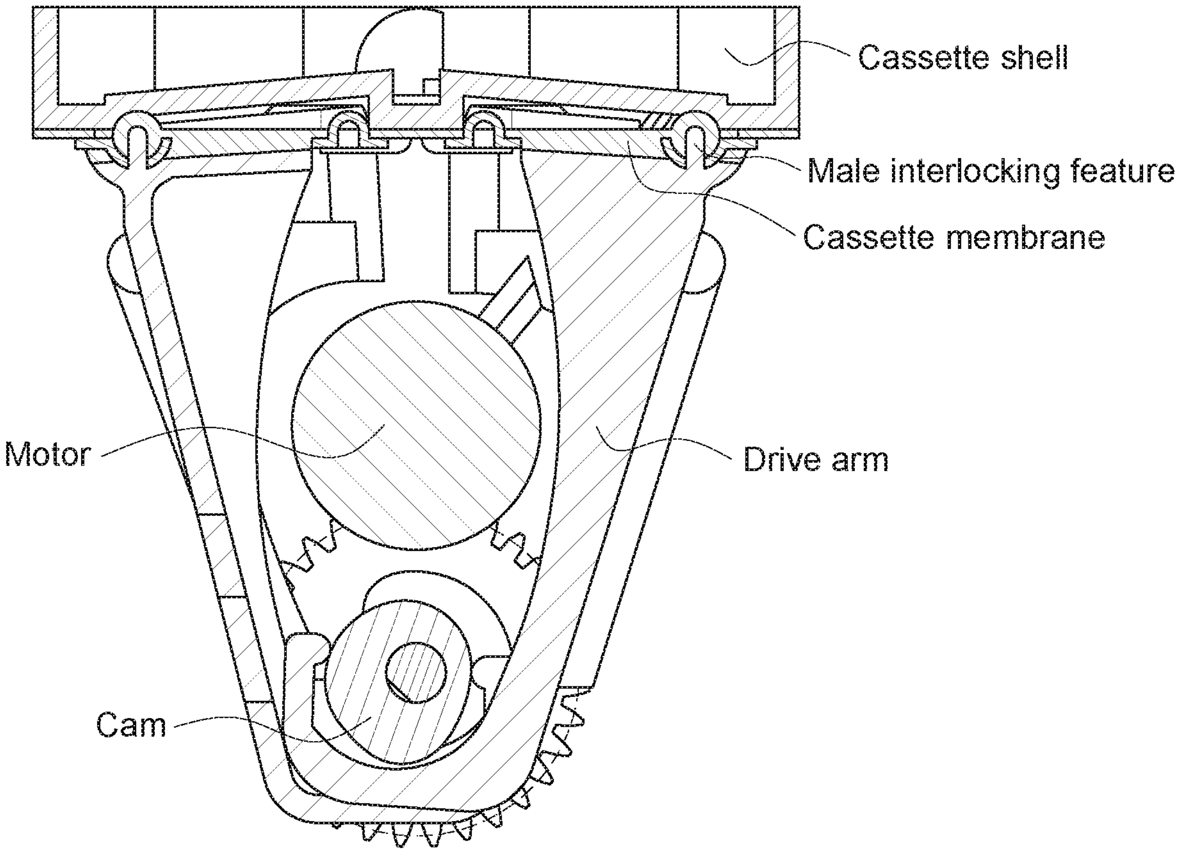
FIG. 1A shows a side view of a pumping system including a pumping mechanism and disposable cassette according to a non-limiting embodiment of the disclosure.
Figure 1B:
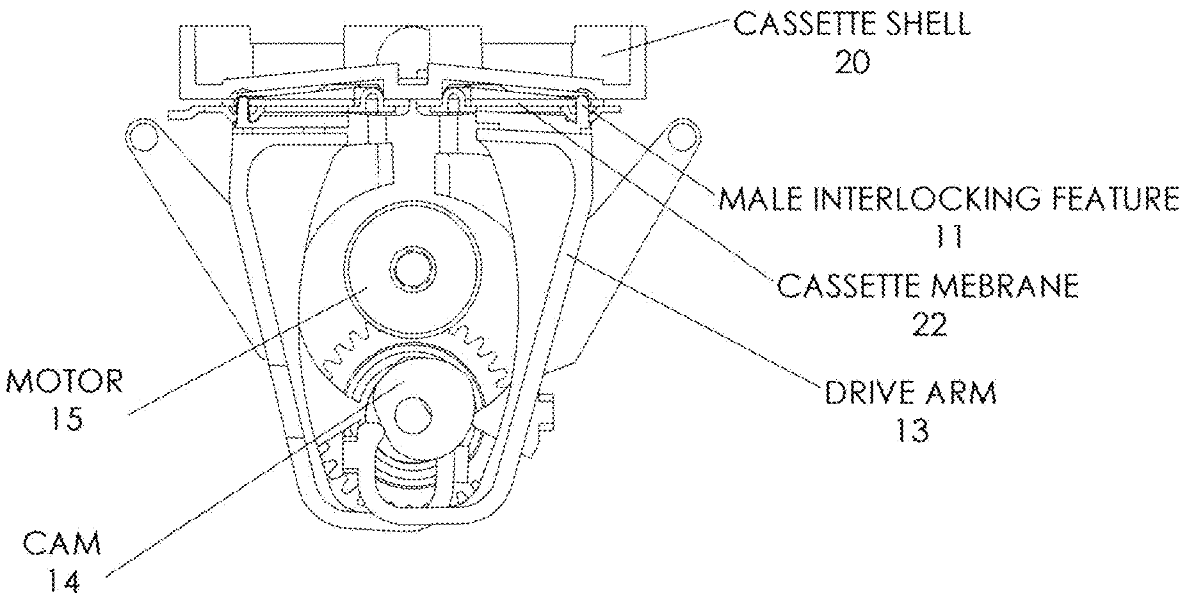
FIG. 1B shows a side view of a pumping system including a pumping mechanism and disposable cassette according to a non-limiting embodiment of the disclosure, which is similar to the system shown in FIG. 1A, wherein some of the similar features to the system shown in FIG. 1A are marked with the same reference characters.

Referring to the non-limiting embodiment shown in FIG. 1A, the main surface of each drive arm 13 that is in contact with the membrane 22 of the disposable cassette 20 has a means for mechanically coupling to the membrane of the disposable cassette. In one embodiment, the means for mechanically coupling can be located orthogonal to the contacting face, centered on the axis of rotation of the drive arms 13, and longitudinal to the axis of flow.

In the non-limiting embodiment shown in FIG. 1A, the means for mechanically coupling is defined by a male interlocking feature 11. In FIG. 1A, the male feature 11 is located orthogonal to the contacting face, centered on the axis of rotation of the drive arms, and longitudinal to the axis of flow of fluid through the disposable cassette. As the disposable cassette 20 is loaded on the pumping instrument, the male features 11 on the drive arms 13 slide into corresponding slots in the membrane 22 of the disposable cassette 20. As a drive arm 13 rotates during a fill cycle, the male feature 11 serves to pull the disposable membrane back, creating a vacuum, and pulling fluid into a chamber of the disposable cassette. The disposable cassette can be the cassette 20 shown in FIGS. 2A-2C, which is disposable cassette having improvements compared to the disposable cassette 200 shown in FIGS. 6A and 6B.

Figure 2A:
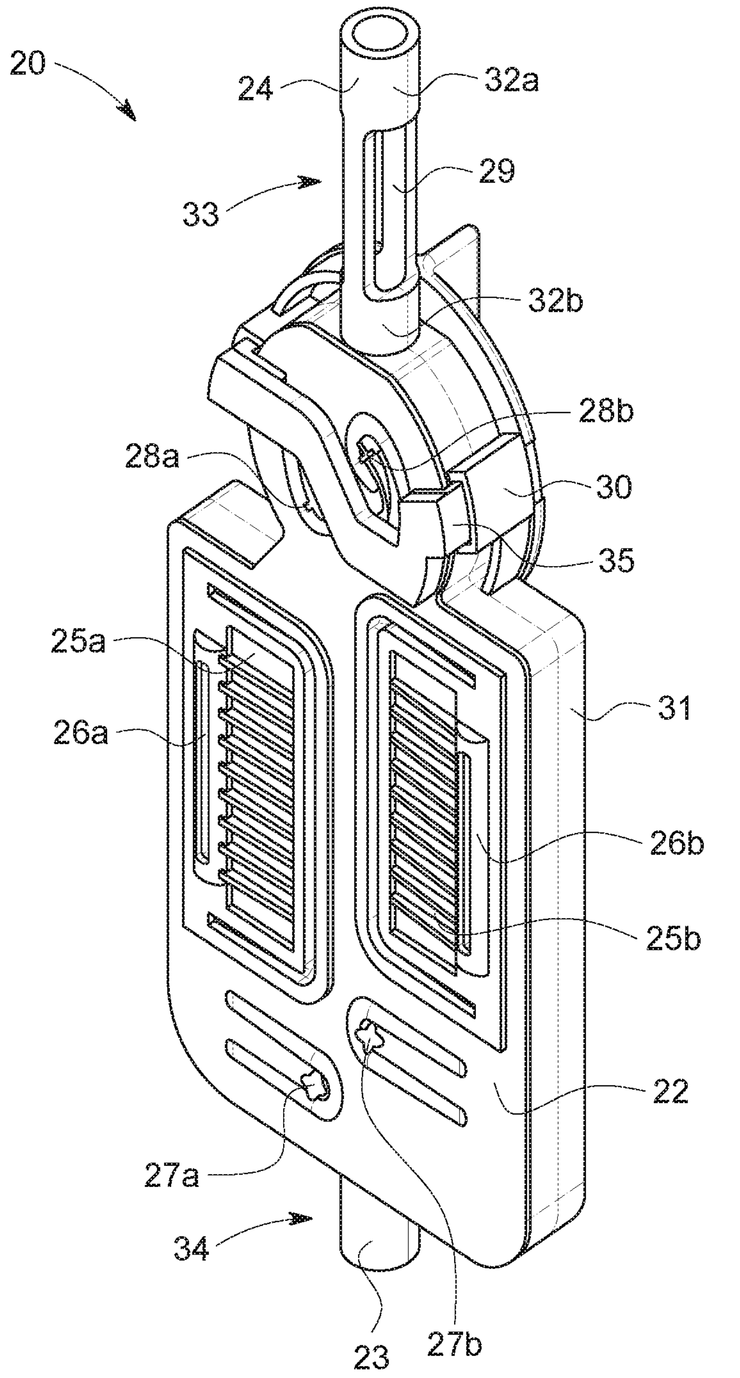
FIG. 2A shows a perspective view of the membrane side of a disposable cassette according to a non-limiting embodiment of the disclosure.
Figure 2B:
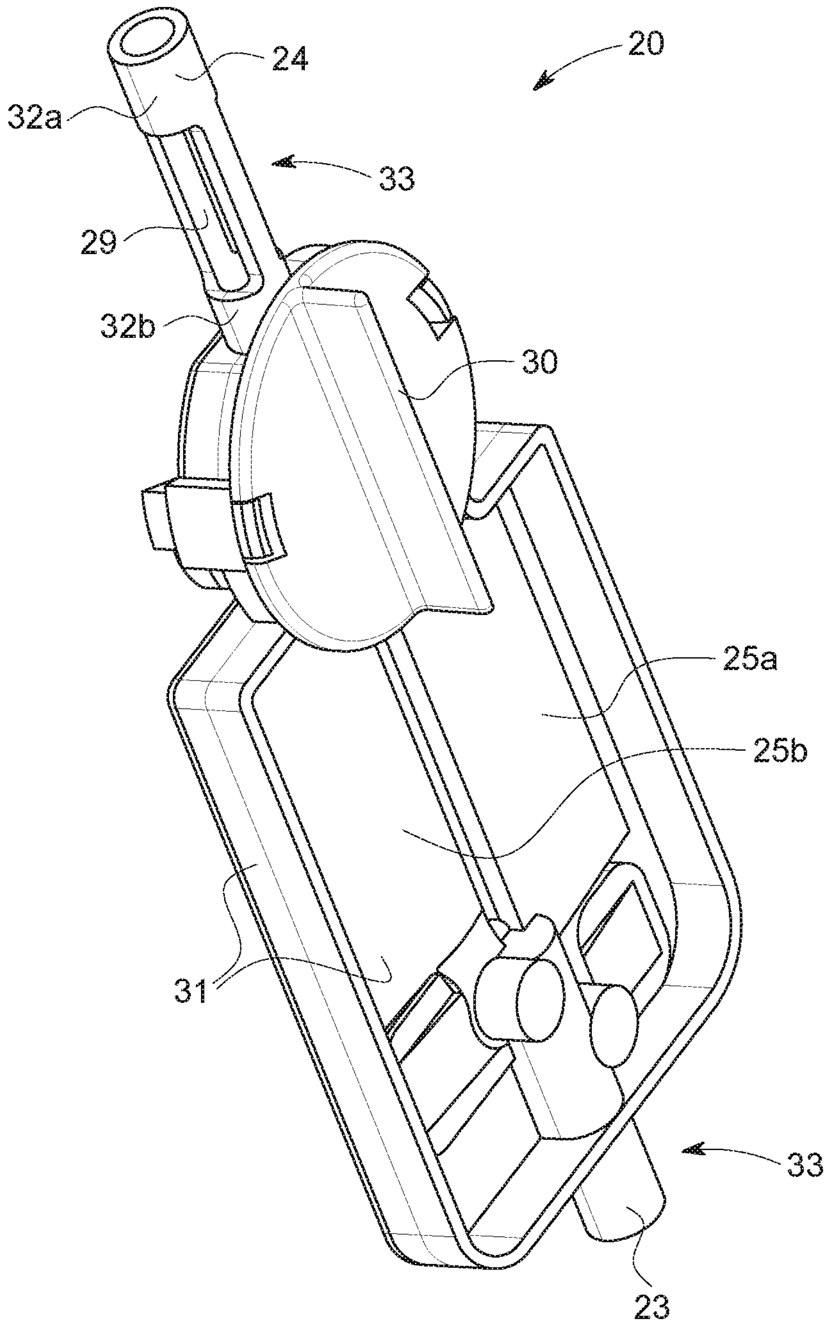
FIG. 2B shows a perspective view of the shell side of the disposable cassette shown in FIG. 2A according to a non-limiting embodiment of the disclosure wherein the flow stop is in an open position.
Figure 2C:
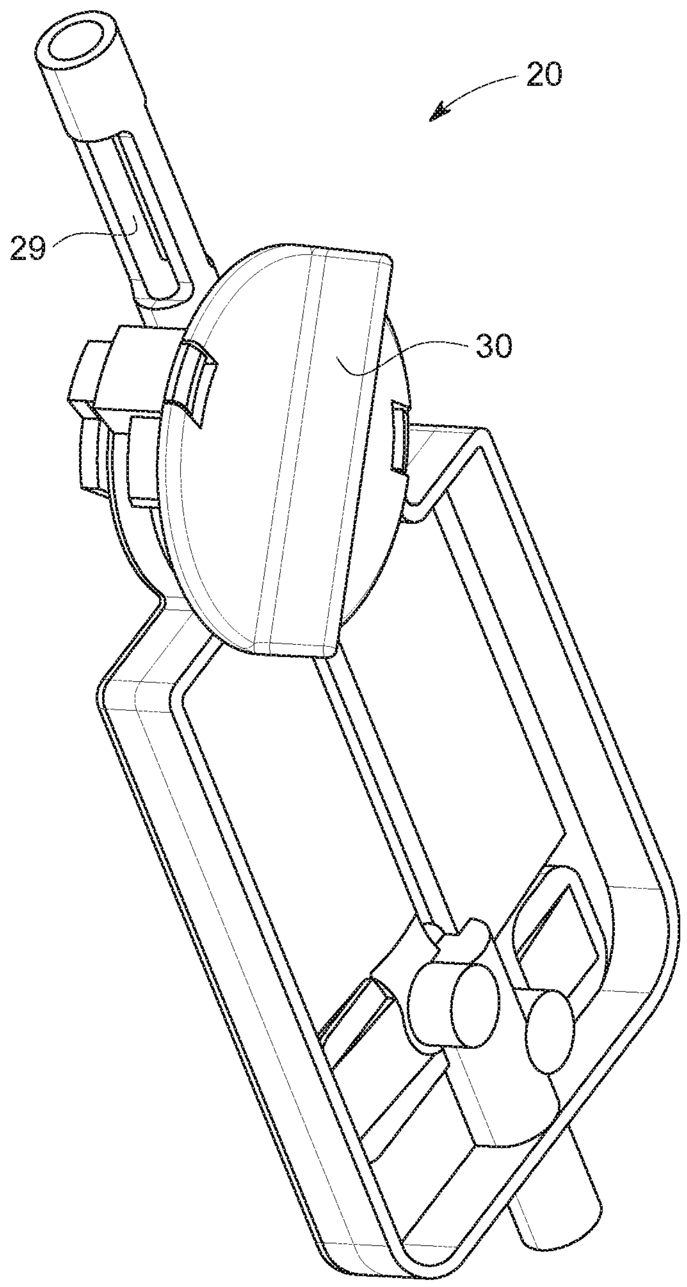
FIG. 2C shows a perspective view of the shell side of the disposable cassette shown in FIG. 2A according to a non-limiting embodiment of the disclosure wherein the flow stop is in a closed position.
Figure 2D:
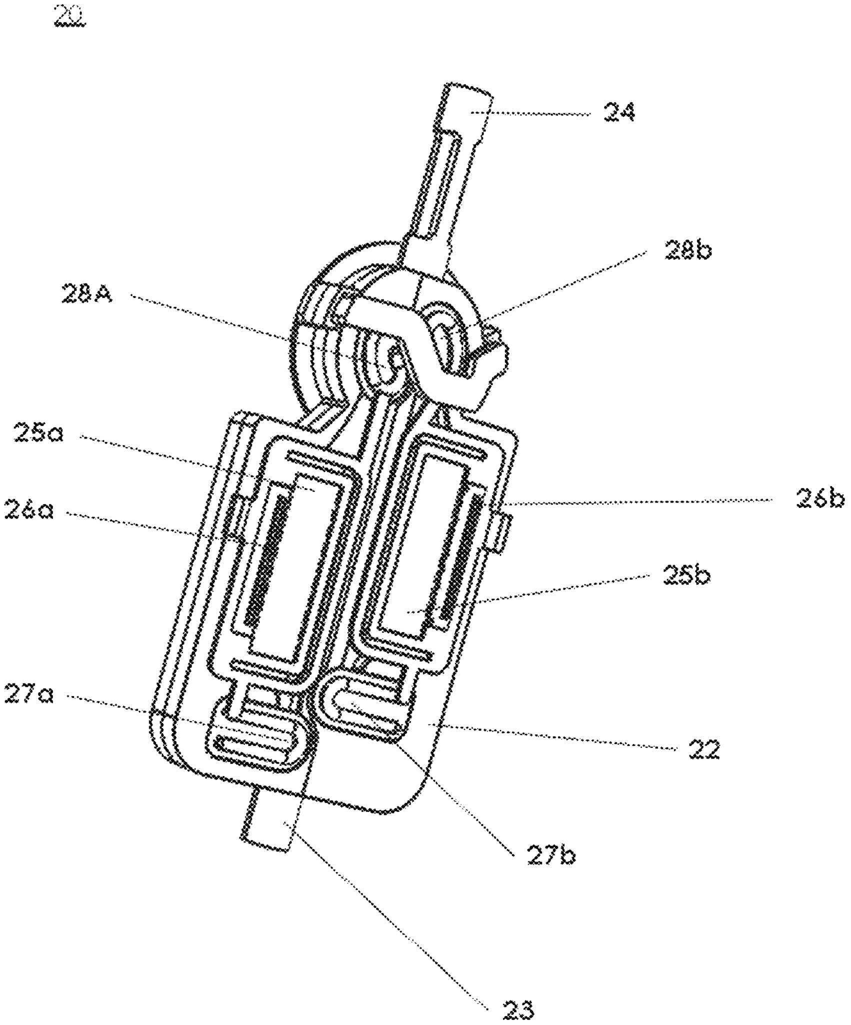
FIG. 2D shows a perspective view of the membrane side of a disposable cassette according to a non-limiting embodiment of the disclosure, which is similar to the cassette shown in FIG. 2A, wherein some of the similar features to the disposable cassette shown in FIG. 2A are marked with the same reference characters.
Figure 2E:
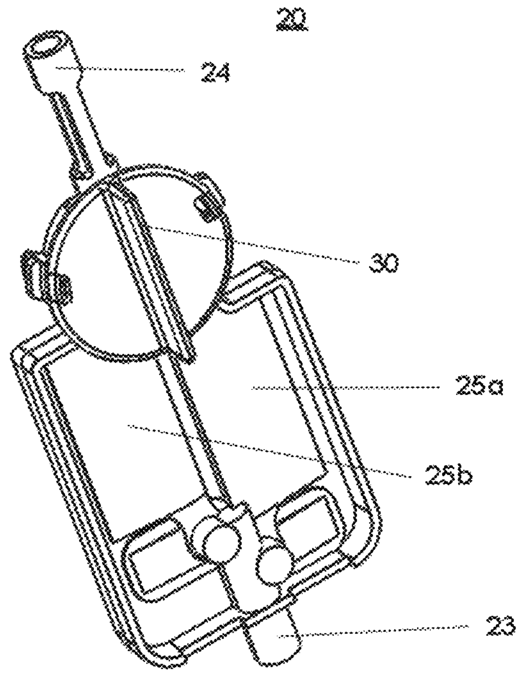
FIG. 2E shows a perspective view of the shell side of a disposable cassette according to a non-limiting embodiment of the disclosure, which is similar to the cassette shown in FIG. 2B, wherein some of the similar features to the disposable cassette shown in FIG. 2B are marked with the same reference characters.
Figure 2F:
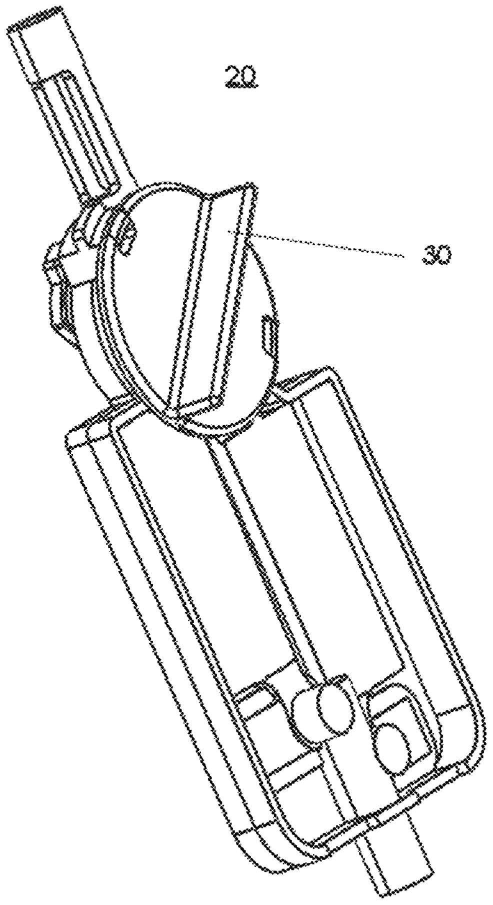
FIG. 2F shows a perspective view of the shell side of a disposable cassette according to a non-limiting embodiment of the disclosure, which is similar to the cassette shown in FIG. 2C, wherein some of the similar features to the disposable cassette shown in FIG. 2C are marked with the same reference characters.

FIGS. 2A-2C show perspective views of a disposable cassette 20 useable with the non-limiting embodiments described herein. The disposable cassette 20 includes similar features to the disposable cassette 200 of Patent Document 1, including a shell 31 that includes an open bottom side (not labeled), a membrane 22 sealing the open bottom side, a proximal fitment (see arrow 34) having an inlet port 23 at a proximal end thereof, a distal fitment (see arrow 33) having an outlet port 24 at a distal end thereof, and first and second pumping chambers 25*a*, 25*b* (located below the membrane 22 on opposing sides of a central axis of the cassette 20 extending between the inlet and outlet port). The disposable cassette 20 also includes first and second inlet valves 27*a*, 27*b* (each in fluid communication with the inlet port 23), and first and second outlet valves 28*a*, 28*b* (each in fluid communication with the outlet port 24). In a non-limiting embodiment, the first and second pumping chambers 25*a*, 25*b* have an equal volume. A general discussion of the operation of these elements of the cassette 20 is described in Patent Document 1, which is incorporated by reference in its entirety. The view in FIG. 2A is of the open bottom side of the cassette, which is sealed by the membrane 22, while the view in FIG. 2 is of the reverse side of the cassette, which is the closed side (or shell side).

As shown in FIGS. 2A-2C, the cassette 20 may also include a flow stop 30, which is a user actuated means for opening and closing the fluid pathway by rotating the flow stop 30. FIG. 2B shows a non-limiting embodiment where the flow stop 30 is in an open position, thereby allowing fluid to flow through the outlet port 24. FIG. 2C shows the flow stop in a closed position, thereby stopping fluid from flowing through the outlet port 24. In an alternative non-limiting embodiment, the flow stop 30 could be located at the inlet end of the cassette. In the non-limiting embodiment shown in FIGS. 2A-2C, the flow stop 30 can be activated by a ¼ twist of knob (unlabeled) of the flow stop 30 by the user. In another non-limiting embodiment, the flow stop 30 could be omitted from the cassette 20.

As shown in FIG. 3A, the flow stop 30 can be connected to an actuating beam 35, which can be fixed on the opposing side of the cassette 20 and functions to control both outlet valves 28*a*, 28*b*. FIG. 3A, shows the flow stop 30 in the open position, and thus the outlet valves 28*a*, 28*b* are not closed by actuating beam 35, FIG. 2C shows the flow stop in the closed position which closes outlet valves 28*a*, 28*b* and allows the cassette 20 to be loaded into pump 10.

In a non-limiting embodiment, based on the structural configuration of the flow stop 30 and the corresponding structural configuration of the case bezel 19 of the pumping mechanism 10, the cassette 20 can only be loaded (i.e., attached or coupled) to the pump 10 when the flow stop 30 is in the closed position. Once loaded, the knob of the flow stop 30 can then be rotated to an open position. This is shown, for example, by the progression of loading exemplary cassette 20 into the exemplary bezel 19 of case 60 in FIGS. 8D to 8F.

As shown in FIGS. 2A-2C, the cassette 20 can include opposing cutouts 29, discussed in more detail below, located just proximal to the outlet port 24 for facilitating an AIL detection system.

Figure 3B:
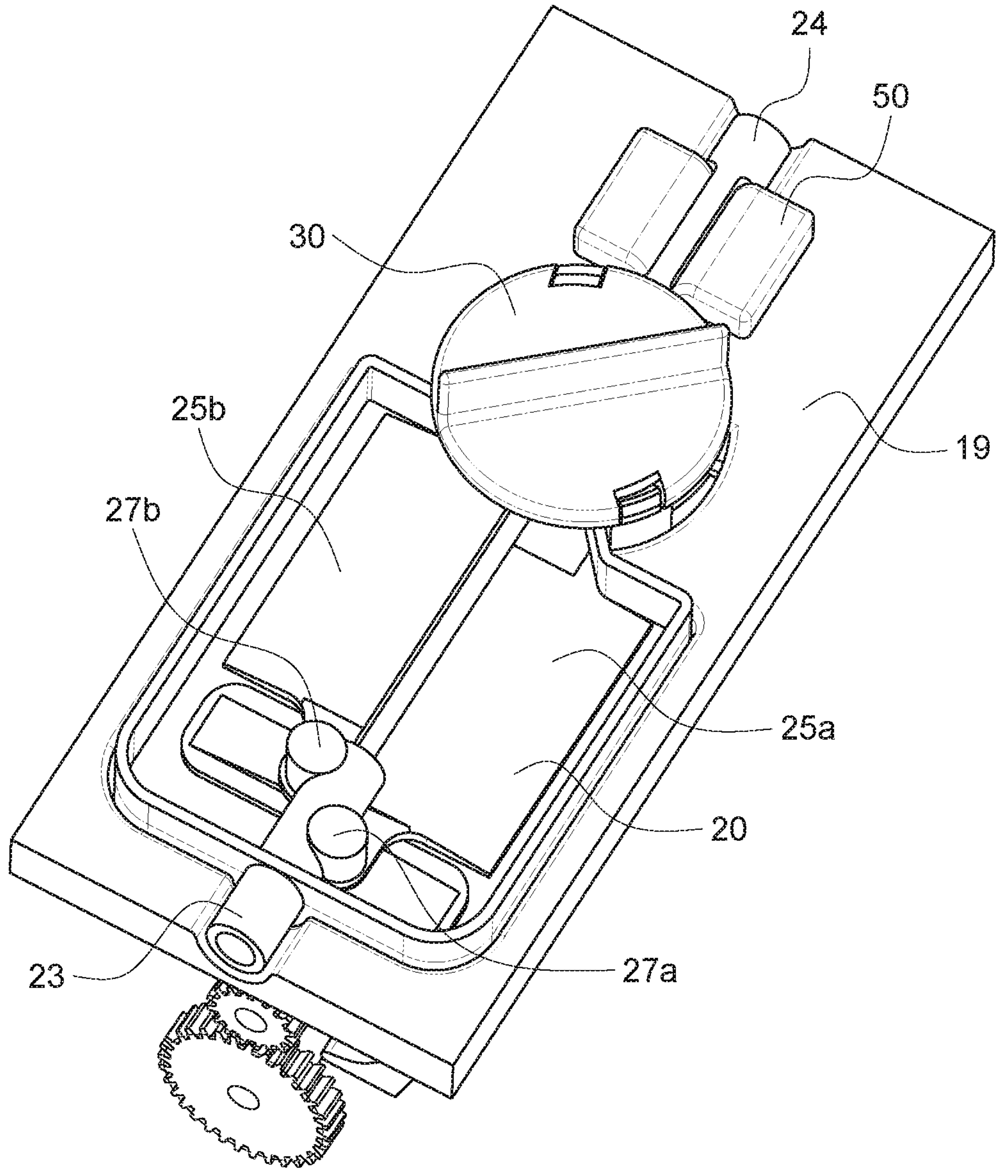
FIG. 3B shows a perspective view of a disposable cassette attached to the pumping mechanism of FIG. 3A according to a non-limiting embodiment of the disclosure.

FIG. 3B shows an example of how the disposable cassette 20 shown in FIGS. 2A-2C could be attached or coupled to chassis of the pumping mechanism 10 shown in FIG. 3A. In FIG. 3B, the membrane 22 sealing the open bottom side of the disposable cassette 20 is facing downward and the closed top side (or shell side) of the cassette is exposed. Further, FIG. 3B also shows that, in a non-limiting embodiment, the AIL sensor 50 can be shaped for mating with the cutouts 29 section at the outlet end of the cassette 20, as discussed in more detail below.

FIG. 3B also shows that, in a non-limiting embodiment, the cassette may have a shape that is not symmetrical on the sides of an axis extending between the inlet port 23 and the outlet port 24. This is for safety and convenience, as it allows, for example, the operator to quickly and easily attach the cassette 20 to the pumping mechanism 10 in the correct manner, since the cassette in this non-limiting embodiment can only be attached or loaded in one spatial orientation relative to the pumping mechanism. When cutouts 29 for mating with the AIL sensor 50 (e.g., an ultrasonic transducer pair) are included in the cassette 20, this also facilitates this type of one-way attachment. This is shown, for example, in the cassette loading progression shown in the non-limiting embodiment of FIGS. 8D-8F.

The male interlocking feature 11 may be defined, for example, by a blade, a rib or a vane positioned longitudinal to the axis of flow, orthogonal to the flat surface area of the drive arm 13 contacting the disposable cassette 20 and centered on the axis of rotation. The fact that the drive arm 13 rotates allows the concept to work. Because the male feature 11 is inserted into a mating female feature as the disposable cassette 20 is loaded, the back face of the male feature 11 pulls a rigid section of the disposable cassette 20 back during the filling cycle. Furthermore, in a non-limiting embodiment, the drive arm 13 can be tapered from base to tip to match the draft of the mating feature in the disposable cassette 10 to facilitate loading.

As shown in FIG. 3A, the male interlocking feature 11 may include blades 11*a* and 11*b*, wherein one blade is positioned on each of the two drive arms 13*a*, 13*b*.

FIG. 4 shows another non-limiting embodiment of a drive arm 13 in mechanical communication on one end with a cam 14 and having a blade 11 on the other end. In FIG. 4, the blade 11 is in a position that will be orthogonal to the contacting face of the cassette and longitudinal to the axis in which fluid will flow through the disposable cassette.

The disposable cassette 20 may have a corresponding female feature for coupling with the male interlocking feature 11 of the pumping mechanism 10. The female feature may be a tapered or drafted recess often used to generate a zero clearance or line to line fit between two removable components. Examples would include ground glass stoppers in chemical storage bottles, gibs used to take up clearance between moving components in precision equipment and collets used to center and hold cutting tools on machinery equipment.

In a non-limiting embodiment, as shown in FIG. 2A, the female feature may be slots 26*a* and 26*b*. Each slot 26*a*, 26*b* independently corresponds to (and is disposed over) one of the dual pumping chambers 25*a*, 25*b* of the cassette that is sealed by the membrane. When the cassette is loaded on to the pumping mechanism, the blades 11*a* and 11*b* respectively slide into mating slots 26*a* and 26*b* of the disposable cassette 20, thereby facilitating a mechanical coupling.

Since the drive arms 13 operate 180 degrees out of phase, the blades 11*a*, 11*b* should align and mate with their respective slots 16*a*, 16*b* at any point in the pumping cycle. To accomplish this, the width of the slot opening, can be set larger than the tip of the blade to accommodate the range of variation in rotational position between the cassette and drive arms. This allows the disposable cassette to be loaded and unloaded multiple times without damage.

In addition, the physical cross section of the blades 11*a*, 11*b* can be designed to minimize deflections between the drive arms 13 and cassette 20 when the drive arms 13 rotate back to pull fluid into the pumping chambers of the disposable cassette 20. This allows the male interlocking feature, e.g., the blades 11*a*, 11*b*, to be made using a variety of manufacturing processes and different materials from machined aluminum or stainless steel to injection molded plastic.

A material of the membrane 22 of the cassette is not particularly limited. Exemplary materials include polymers, in particular, a thermoplastic elastomer, such as a polyvinylchloride, a high-density polyethylene, and a polyurethane. However, the material is not limited to any of the six generic classes of commercial thermoplastic elastomers and not classified thermoplastic elastomers.

In a non-limiting embodiment, the membrane is a single layer of an elastomeric material. Alternatively, the membrane could be a multi-layer structure wherein an inner layer that is exposed to the pumping chambers is made of a polymer material that is different from a polymer material of an outer layer.

A material for the female feature of the cassette is not particularly limited and could be, for example, the same material as the membrane. Alternatively, exemplary materials for the female feature include but are not limited to any of the six generic classes of commercial TPEs and not classified thermoplastic elastomers Mechanically coupling the disposable cassette 20 to the pumping mechanism in a manner described herein can improve the operation of the pumping system described in Patent Document 1 and can reduce the functional burdens normally shouldered by the membrane of the disposable cassette. For example, the membrane 22 of the disposable cassette 20 is not stressed or depended on to provide the force required to draw fluid into the pump. The disposable cassette 10 is fully supported by the pumping instrument. In addition, volume stability is controlled by the pumping instrument, not the disposable cassette. The volume of fluid pumped during each revolution of the pumping mechanism of the pumping instrument is unaffected by run time, changes in program delivery rate, fluid viscosity temperature or changes in pressure.

Furthermore, the cassette membrane incorporates features that maintain intimate contact with the articulating elements of the pump mechanism for facilitating efficient, accurate and uniform delivery of fluids. This interface also offers a straightforward and accurate approach to solving inherent problems with existing fluid delivery systems: specifically, the inability to maintain rate accuracy and flow continuity of the drug being delivered.

In an alternative embodiment, the means for mechanically coupling that is provided on the drive arms could also be defined by a female interlocking feature, and the disposable cassettes would then be configured with corresponding male means for mechanically coupling.

By the mechanical coupling, the primary function of a thermoplastic elastomeric material used as the material of the membrane of the disposable is to seal the fluid path, which keeps stresses on the elastomer very low. Further, relaxation of the elastomer over time will not be a factor and does not contribute to pressure sensing drift or effect accuracy. Further, hysteresis can be effectively eliminated by using very compliant thermoplastic elastomeric materials for the membrane of the disposable.

System level problems addressed by the non-limiting embodiments are described below.

Volume accuracy is the most commonly referenced performance metric for an infusion device. It is a measure of the difference between the actual fluid delivered over a prescribed time and the desired, or programmed, volume to be delivered. Pump to pump variation in rate accuracy is driven by manufacturing tolerances in the instrument, disposable component and instrument disposable interface. Because instruments are produced in relatively low volumes, compared to the disposable set, it is advantageous to control tolerances in the critical to function components in the instrument as opposed to the disposable. The disposable is a compliant elastomer manufactured in high volume. It is unstable, difficult to inspect and control dimensionally during manufacture. The non-limiting embodiments described herein remove the disposable cassette from the tolerance loop and reduce the number of critical to function components in the mechanism. The total volume pumped each cycle is determined only by the eccentricity of the cam and the net surface area of the drive arm in contact with the disposable membrane.

Changes in the rate of fluid delivery over the course of an infusion are driven by the instability of the elastomeric material in the disposable cassette and the overall sensitivity of the pumping mechanism to changes in external operating conditions. The volume delivered during each pumping cycle needs to be stable. Elastomers will expand or contract, much like a balloon, with changes in pressure. The volume of fluid displaced each pumping cycle therefore, becomes a function of the differential pressure across the pump. The greater the pressure upstream, feeding the pump, the larger the tubing cross section and the greater the volume of fluid that is pumped per cycle. The opposite is true if the pump is working against a negative head height or upstream vacuum.

Changes in rate accuracy can also occur over the course of an infusion. Pumping segments and cassette membranes in use today are subject to high levels of stress as they are compressed to occlude the fluid path. These high contact stresses cause material breakdown and wear. For this reason, they are currently made with very expensive, high strength, resilient materials. Since the membrane in these non-limiting embodiments is fully supported and not over stressed it remains dimensionally stable over the duration of an infusion, independent of rate.

Volume delivery errors induced by these problems cause accuracy verification testing to be so specific they do not apply to a wide range of common clinical applications. Manufactures' rate accuracy claims often have more to do with specsmanship and product marketing than actual clinical utility. Published claims are made in the context of laboratory controlled operating conditions specified by device manufactures and testing agencies. Accuracy claims are based on pump performance over the range of delivery rates at a specific head height, back pressure, instrument orientation and fluid type. Although pumping rate also affects performance, software corrections to motor speeds are used to mitigate the influence. An additional constraint typically imposed on volume accuracy testing, is that the disposable tubing sets be exercised or "broken in" before a test is run. Data collection begins only after a designated startup period. As mentioned above, the high stress levels seen by the elastomer will cause the volume delivered by a virgin disposable set to decrease during the first few cycles of operation, as the dimensional and physical properties of the elastomer relax. Steady state operation is attained relatively quickly when compared to a syringe pump, however, at low flow rates and, for critical drugs, this change in volume can still be clinically significant.

Flow uniformity is a measure of the variations in the rate of fluid delivery, as opposed to volume accuracy which measures only the total volume of fluid delivered over time. Volume accuracy tests can only measure the average delivery rate over the prescribed collection period. The instantaneous delivery rate for a given instrument could deviate significantly, and still maintain the desired total volume of fluid delivered during the duration of an infusion. It is extremely important that critical drug solutions be administered in a well-controlled, steady delivery rate. Large volume infusion devices, due mostly to the serial nature of the fill and delivery stages of their pumping cycles, have performed poorly in this area, relative to syringe based infusion devices. For this reason, syringe pump instruments are preferred for delivering critical, highly concentrated solutions and for neonatal application. However, the volume of fluid that can be infused is limited to the size of syringe and steady state delivery is achieved only after the compliance and slack in the plunger and instrument are taken up by the drive mechanism. This can be a considerable amount of time, even hours, if you are using a large syringe and a low delivery rate.

The standard measure for flow uniformity is the trumpet curve. Trumpet curves, or "T" curves, represent the maximum percentage deviation from the programmed infusion rate for prime number time intervals, starting at 2 minutes, the shorter the time interval, the greater the positive and negative deviation from the average rate. As the time intervals increase, the positive and negative deviations converge. At 31 minutes, the curves become asymptotic to the nominal infusion rate. The resultant graph looks like the bell of a trumpet. There is work being done to revisit this test, because the body response time to some of the vasoactive drugs is much more rapid than the two-minute window measured. In addition, many infusion devices are driven by stepper motors which rotate in discrete increments. Although, this is not an inherent design issue, step resolution needs to be considered and managed so that the bolus delivered during each motor step and the time interval between steps does not become clinically relevant.

A problem with serial, positive displacement devices in use today is that flow during one pumping cycle is not uniform. As an example, linear peristaltic devices sequentially pinch off the disposable tube, milking the solution downstream. After the last finger closes on the tube, the cycle starts over with the first finger. No actual pumping is done during the transition from the last to first finger. This interval of zero flow is mitigated by running the pump as fast as possible through zero flow phase of the pumping cycle. Pumps that use tandem, chambered cassettes address the end of the pumping cycle, or fill time issue by using a dedicated flow compensation chamber downstream from the primary pumping chamber, which continues pumping fluid as the first chamber fills. This system mitigates the necessity to speed up the mechanism at the end of the pumping cycle; however, it is optimized for uniform flow at only one downstream, patient side, pressure. There is an inherent issue with this approach. Downstream pressure is trapped in the pumping chambers during each pumping cycle, which increases or decreases the volume of the compliant disposable, depending on whether the differential pressure across the pump is positive or negative. This is much the same as the observation on the effects of upstream pressure on peristaltic systems discussed above, however this trapped volume is released upstream when the upstream valve cycles. Flow rate again becomes a function of the differential pressure across the pump. The degree of influence of the pressure differential depends on the volume and compliance of the disposable and instrument.

The dual chamber system described in Patent Document 1 addresses the problems above, and the non-limiting embodiments described herein, for example, improve upon that dual chamber system. For example, the dual chamber system provides continuous delivery. One chamber (25*a* or 25*b*) of the cassette 20 fills as the other chamber (25*a* or 25*b*) pumps. There is no wrap around, or complex rate and pressure dependent algorithm and stepper motor required to provide uniform and uninterrupted delivery of medication to the patient. A constant velocity DC motor can be used which is not only quieter but much more efficient.

Compliance and dimensional instability increase the instrument sensitivity to operating and environmental conditions. Designing a cost effective and accurate fluid delivery system, immune to operational and environment extremes requires, first that critical components of the pumping mechanism reside in the instrument, not the disposable. It is also important that the disposable tubing or membrane wall thicknesses not add to the tolerance stack of components critical to the function and accuracy of the infusion system. In conclusion, this new approach to fluid delivery stems from a design that addresses the inherent issues with products in use today by managing tolerances, stress levels and compliance while taking full advantage of the compounding benefits listed above.

Pressure Sensing Means

Regarding the improved pressuring sensing means, the drive arms of the pumping system described in Patent Document 1, unlike competitive instruments that typically use sliding fingers, pivot around centers just outboard of the two pumping chambers. This new system presents multiple advantages and benefits, which can be further improved by the embodiments disclosed herein.

Figure 4A:
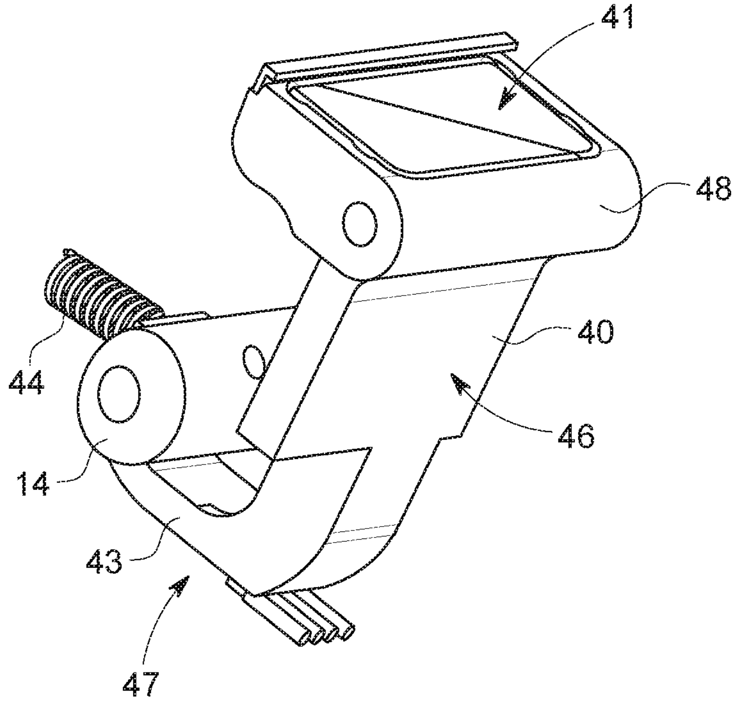
FIG. 4A shows a perspective view of a pumping system drive arm according to a non-limiting embodiment of the disclosure.

FIG. 4A of the present application shows a non-limiting embodiment of a drive arm 40 according to the present disclosure. The drive arm 40 includes a top portion (located near arrow 41), a bottom portion (located near arrow 47), and an intermediate portion (located near arrow 46) connecting the top portion to the bottom portion. The top portion includes a pumping finger 48 that is a plate shape having a surface area (arrow 41) that contacts a disposable cassette coupled to the pumping device. The bottom portion includes a point of contact (see arrow 49 in FIG. 4B) of the drive arm 40 with the cam 14. The point of contact is also seen clearly in FIG. 1A. The bottom portion also includes a beam section 43 connecting the bottom portion of the drive arm 40 to the intermediate portion (arrow 46). In addition, as described, for example, in Patent Document 1, rotation of the cam 14, which is coupled to the drive arm 40 at the point of contact (arrow 49) causes the drive arm 40 to rotate, such that the surface area (arrow 41) of the top portion of the drive arm contacts the membrane of an attached disposable cassette (wherein the surface area (arrow 41) of the top portion of the drive arm 40 corresponds to a cross sectional area of a pumping chamber covered by the membrane at the point of contact between the drive arm and the cassette).

Figure 4B:
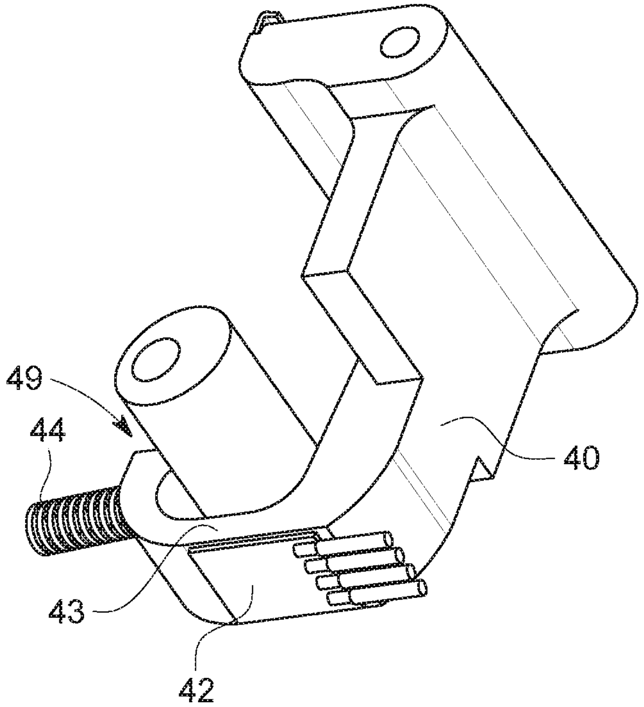
FIG. 4B shows another perspective view of the pumping system drive arm shown in FIG. 4A according to a non-limiting embodiment of the disclosure.
Figure 4C:
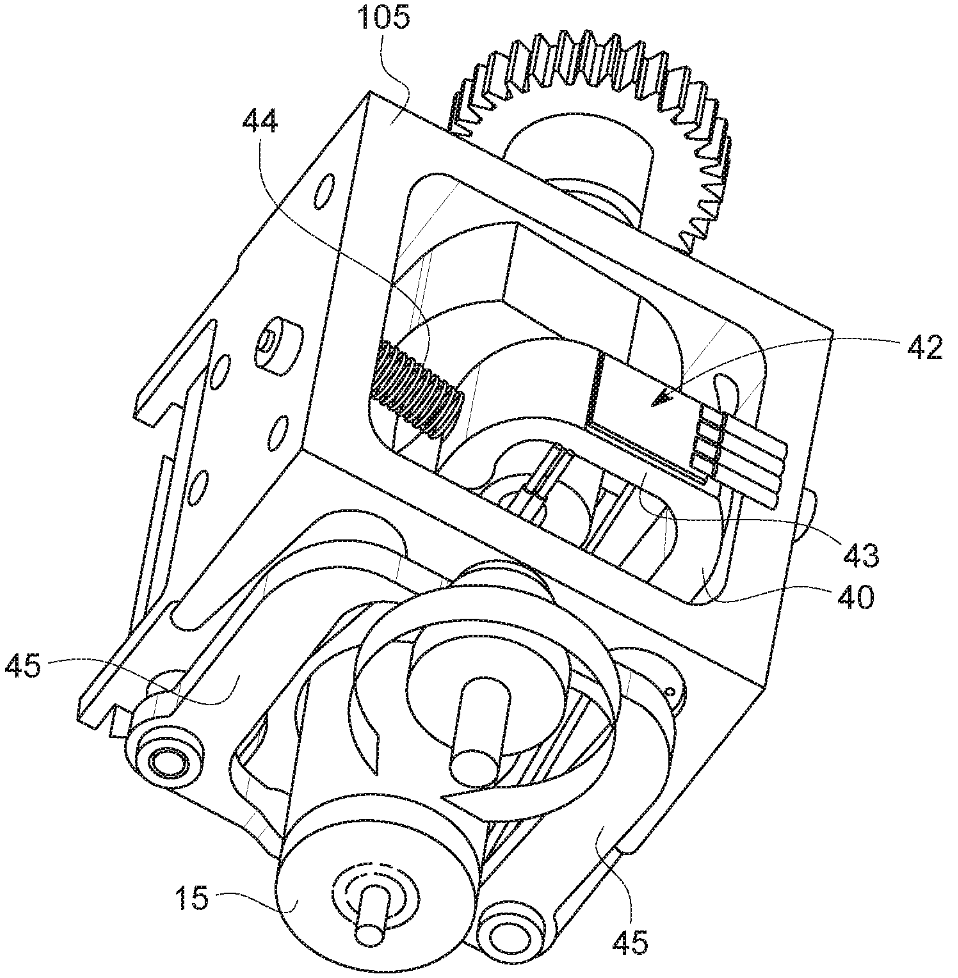
FIG. 4C shows a perspective view of a pumping mechanism according to a non-limiting embodiment of the disclosure that includes two of the pumping system drive arm shown in FIG. 4A.
Figure 4D:
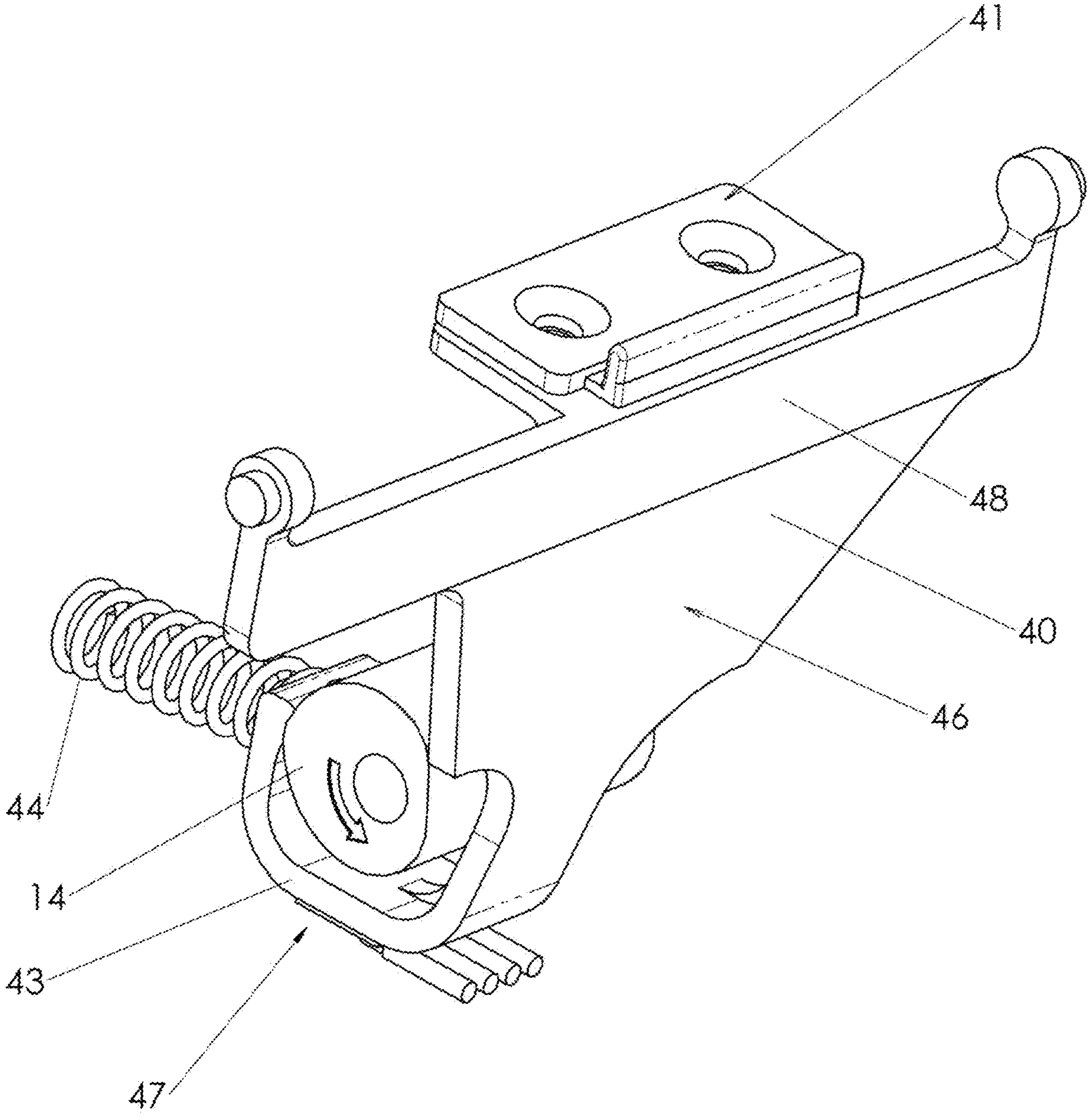
FIG. 4D shows a perspective view of a pumping system drive arm according to a non-limiting embodiment of the disclosure, which is similar to the drive arm shown in FIG. 4A, wherein some of the similar features to the drive arm shown in FIG. 4A are marked with the same reference characters.
Figure 4E:
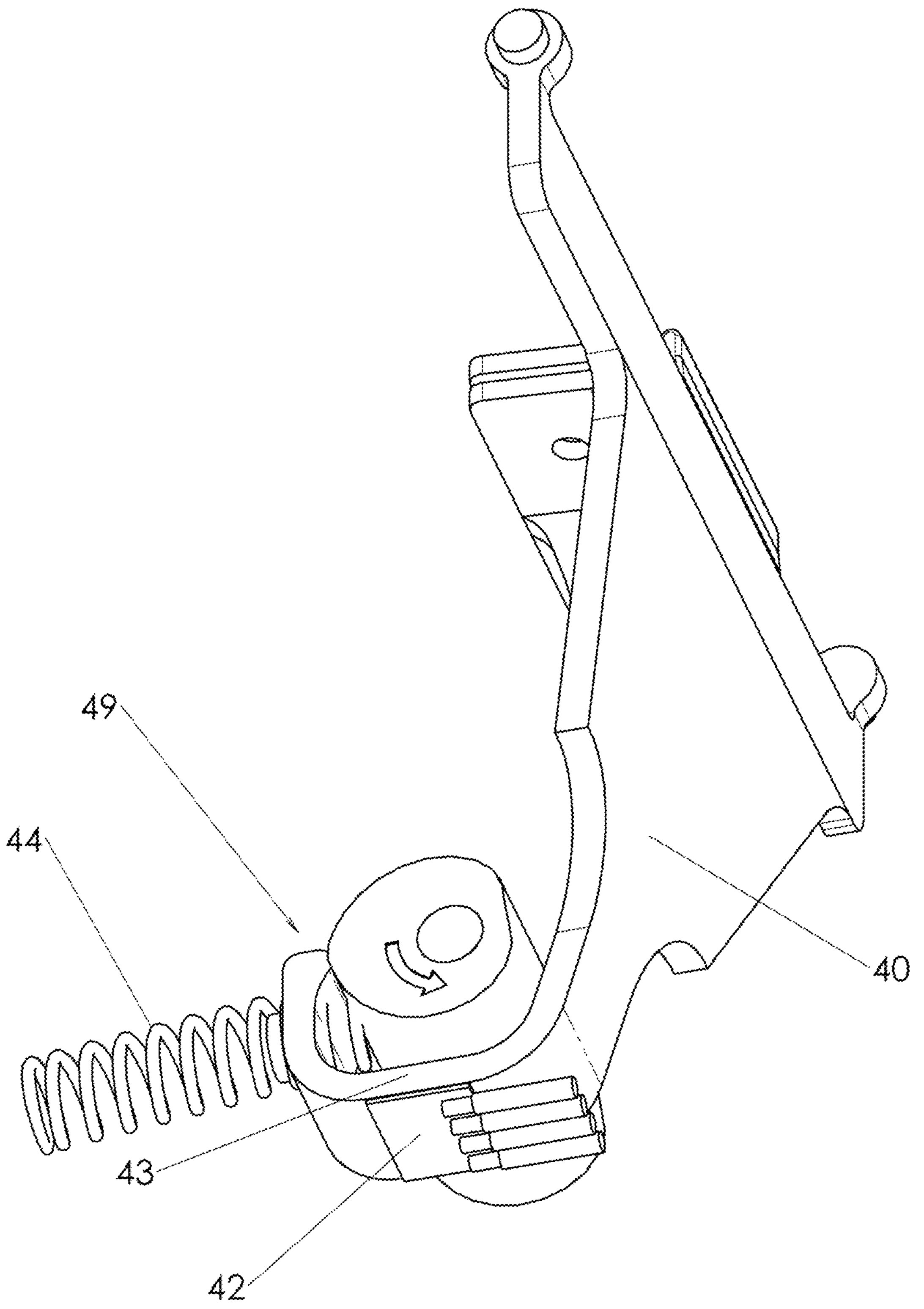
FIG. 4E shows another perspective view of the pumping system drive arm shown in FIG. 4E according to a non-limiting embodiment of the disclosure, which is similar to the drive arm shown in FIG. 4B, wherein some of the similar features to the drive arm shown in FIG. 4B are marked with the same reference characters.
Figure 4F:
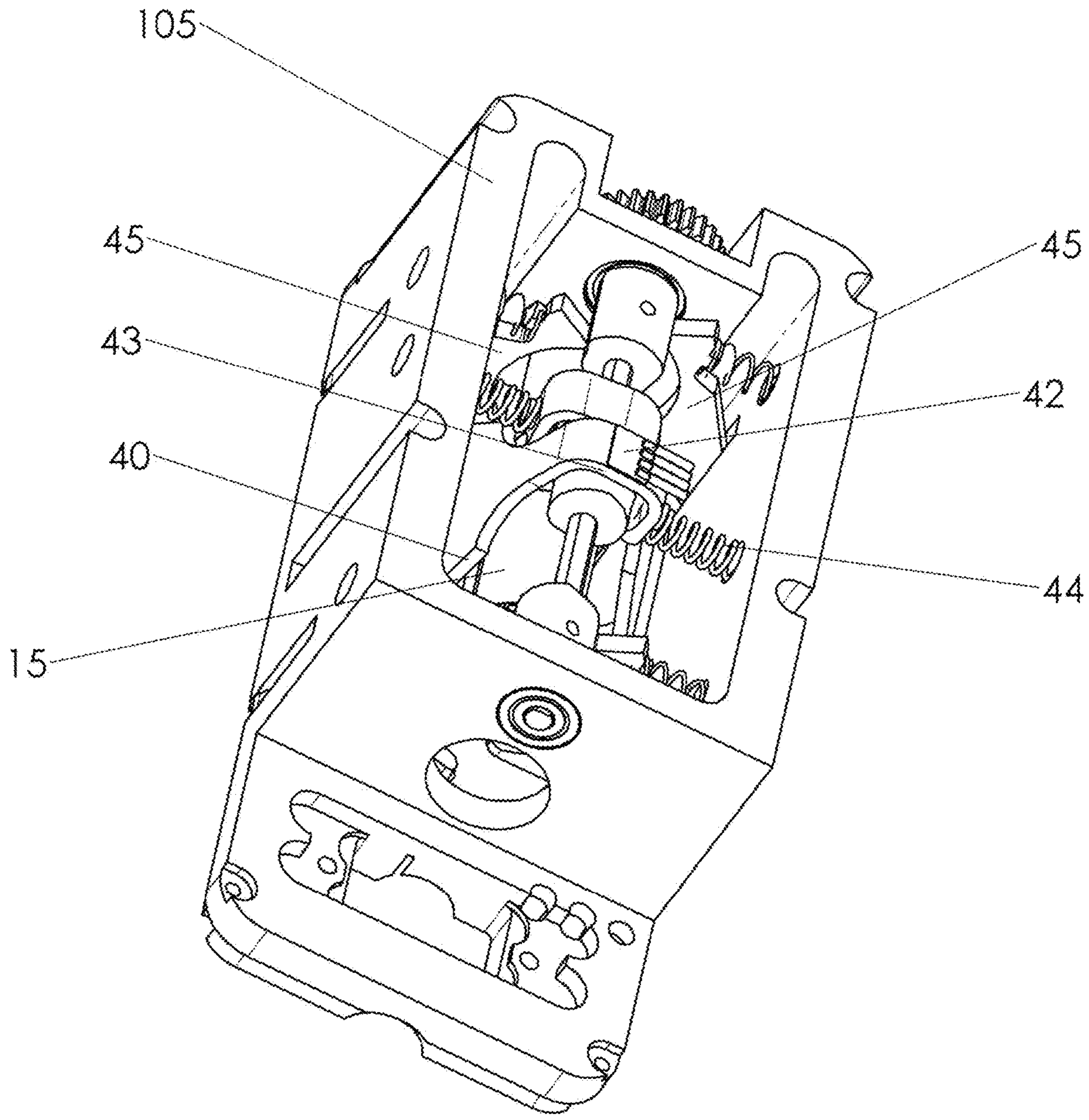
FIG. 4F shows a perspective view of a pumping mechanism according to a non-limiting embodiment of the disclosure that includes two of the pumping system drive arm shown in FIG. 4D, which is similar to the pumping mechanism shown in FIG. 4B, wherein some of the similar features to the pumping mechanism shown in FIG. 4C are marked with the same reference characters.
Figure 5A:
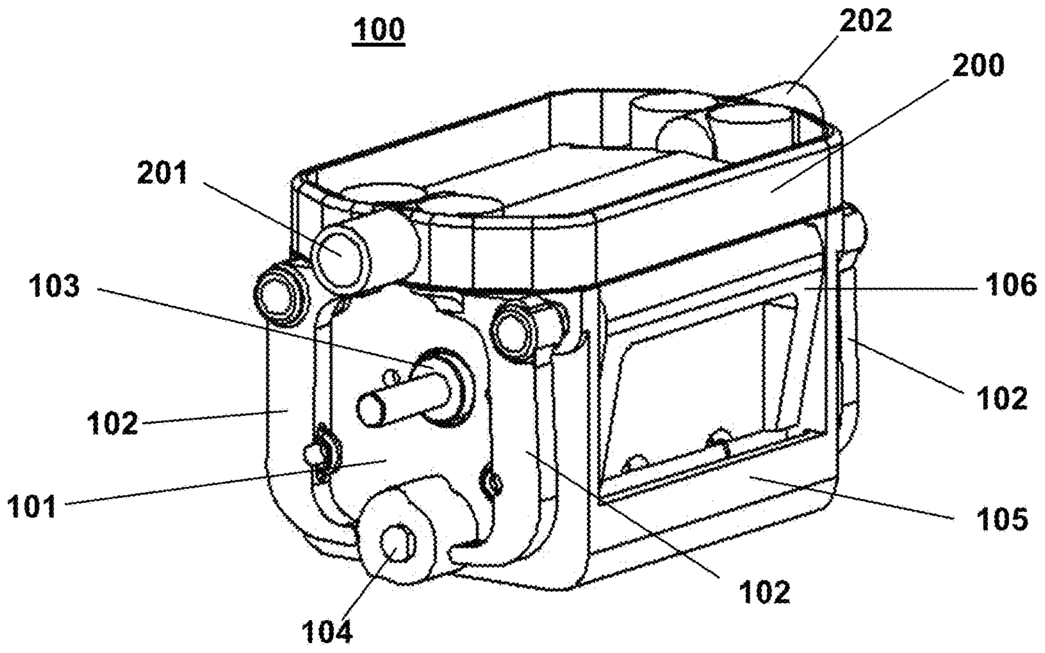
FIG. 5A RELATED ART
FIGS. 5A and 5B are pictorial diagrams showing perspective views of the pumping mechanism and disposable cassette according Patent Document 1.
Figure 5B:
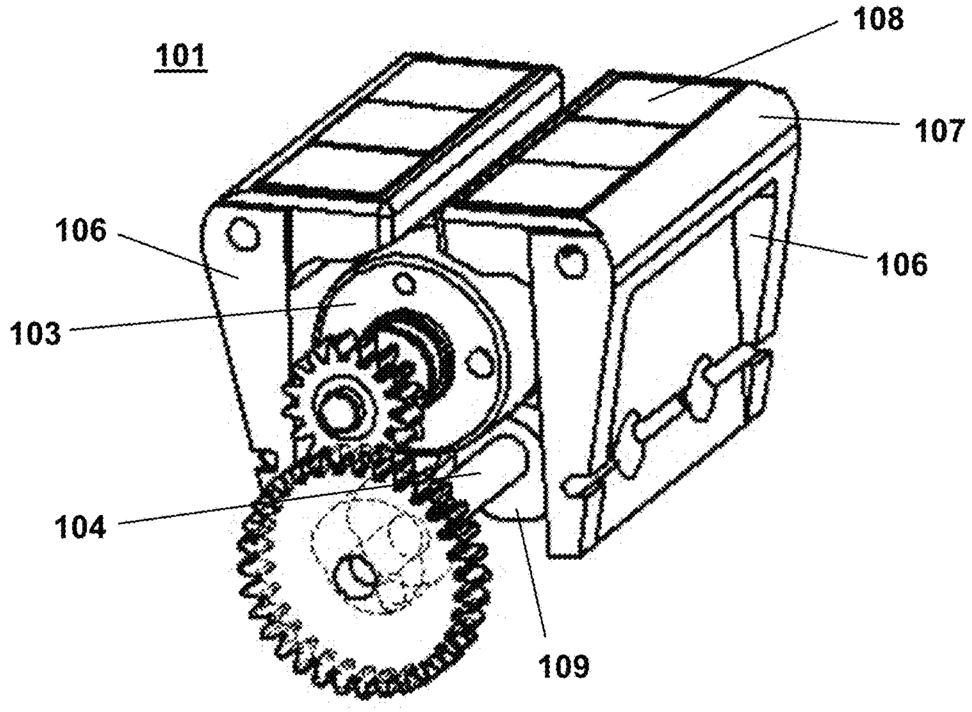
Figure 6A:
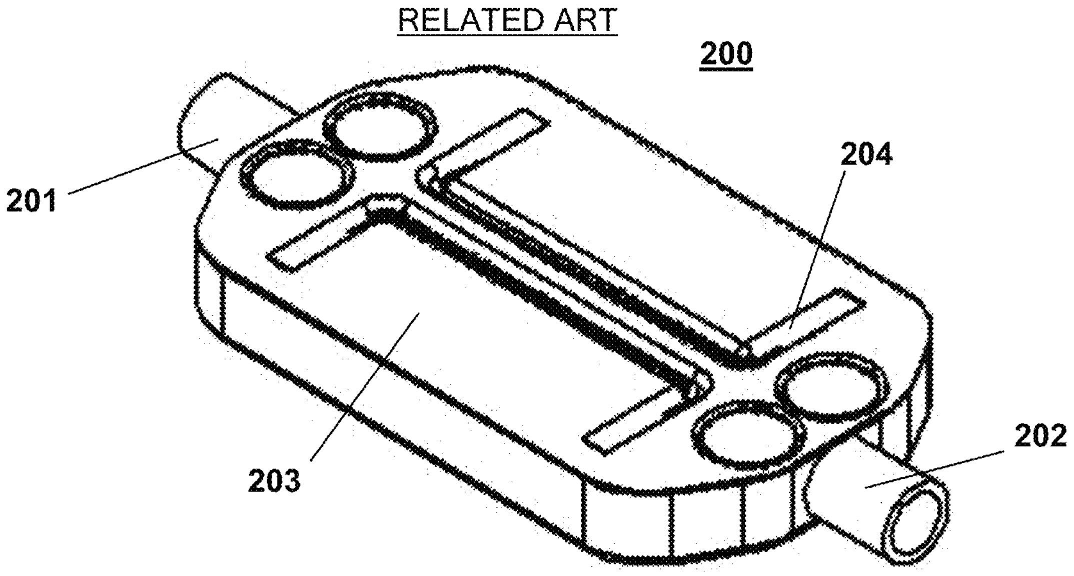
FIGS. 6A and 6B are pictorial diagram showing views of the disposable cassette according Patent Document 1.
Figure 6B:
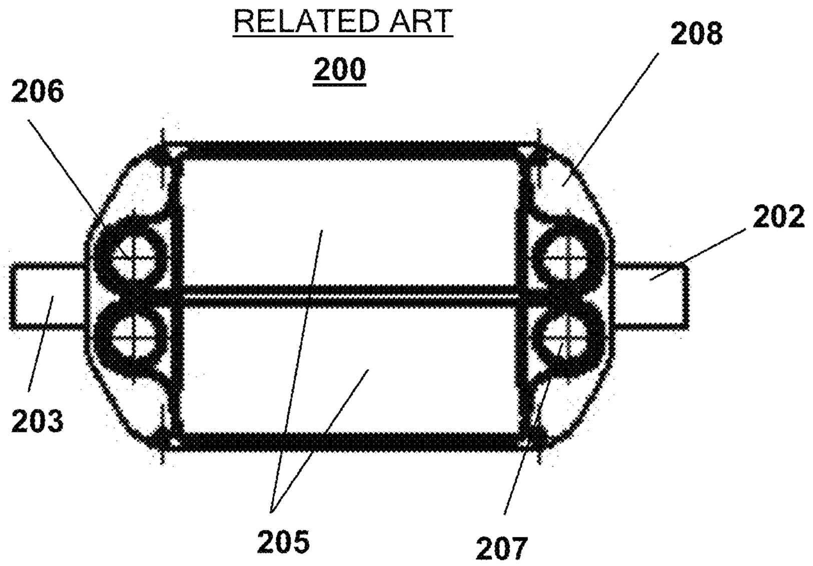
Figure 7A:
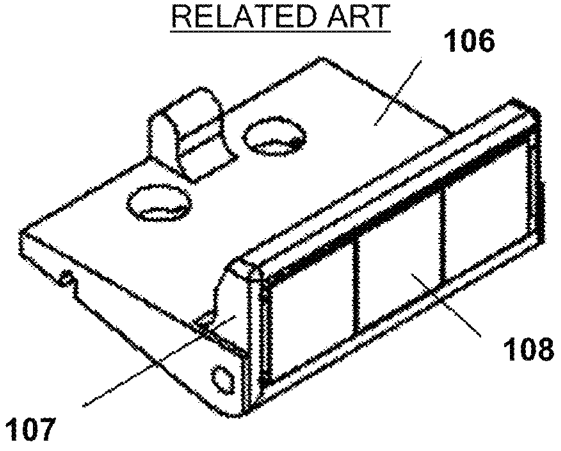
FIG. 7A RELATED ART
FIGS. 7A-7C are pictorial diagram showing views of drive arms according Patent Document 1.
Figure 7B:
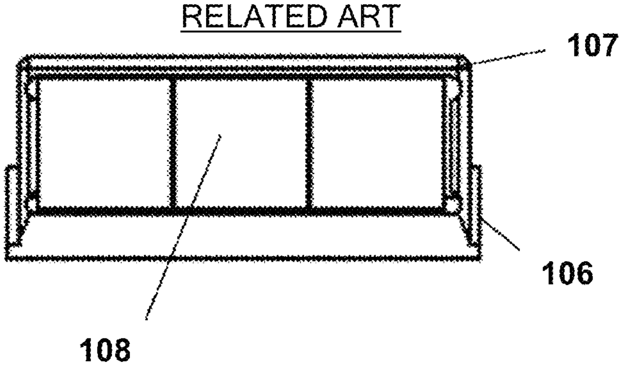
FIG. 7B RELATED ART
Figure 7C:
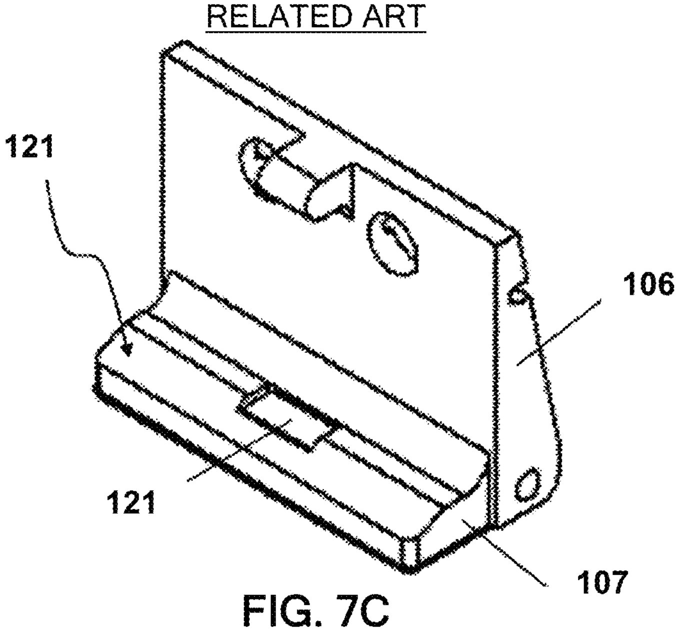

As shown in FIGS. 4A and 4B, in a non-limiting embodiment the beam section 43 has a rectangular cross section.

Figure 3C:
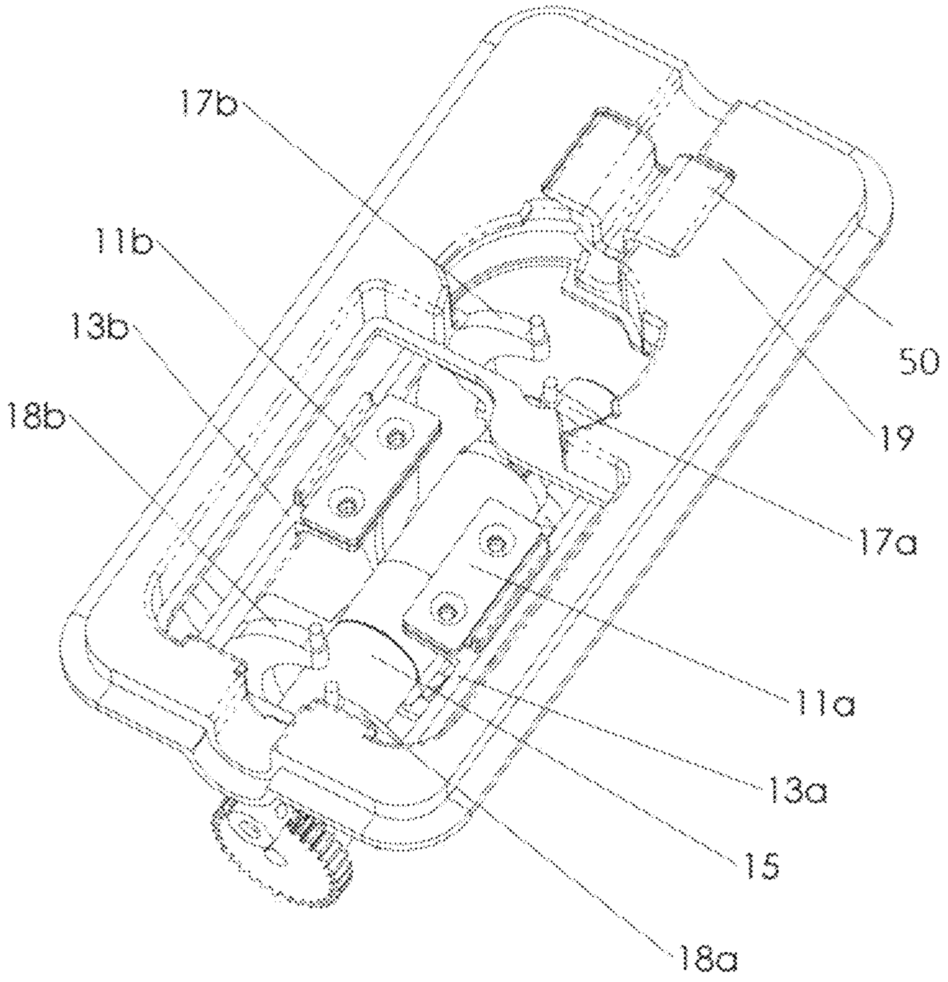
FIG. 3C shows a perspective view of a pumping mechanism according to a non-limiting embodiment of the disclosure, which is similar to the pumping mechanism shown in FIG. 3A, wherein some of the similar features to the pumping mechanism shown in FIG. 3A are marked with the same reference characters.
Figure 3D:
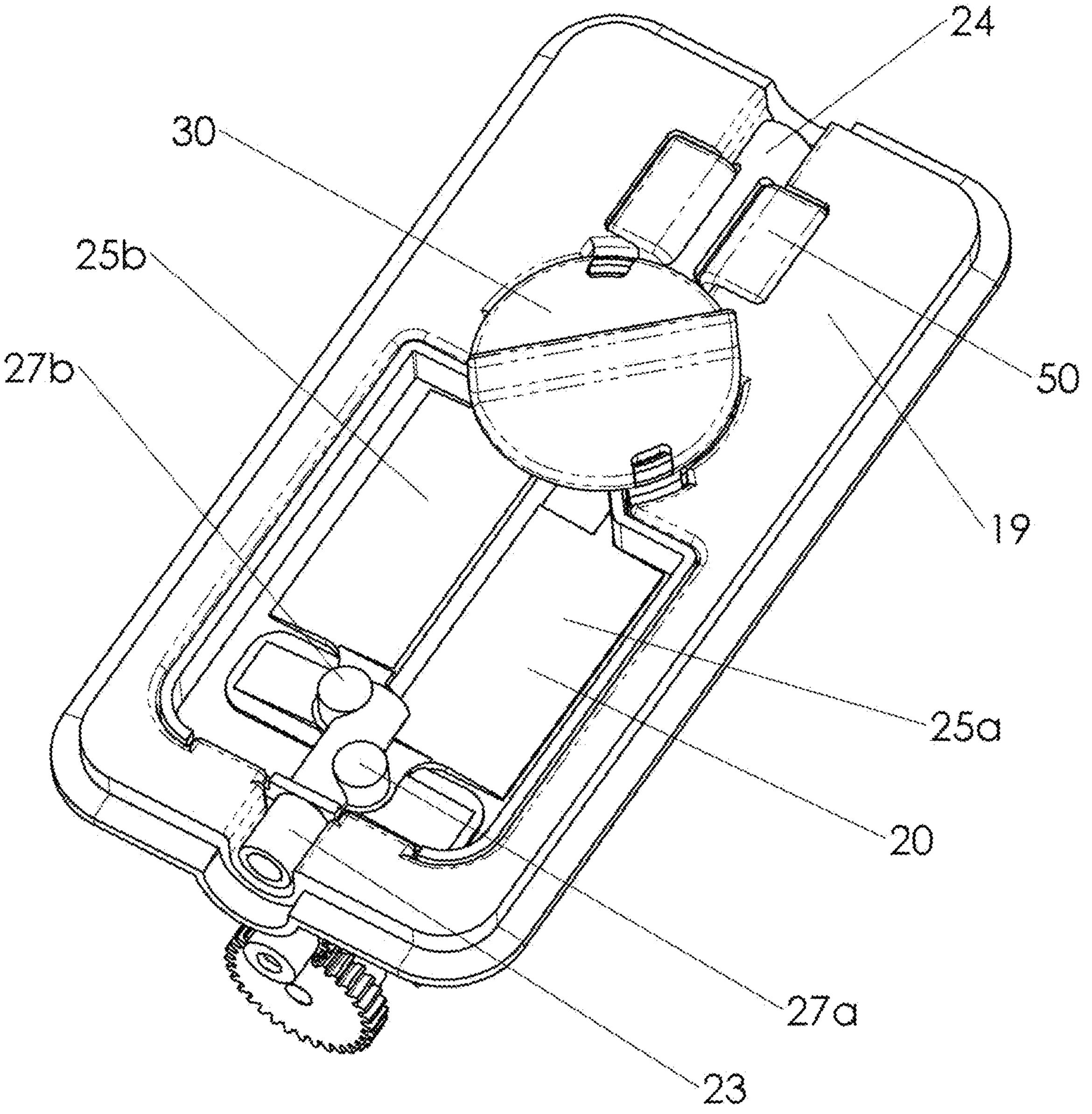
FIG. 3D shows a perspective view of a disposable cassette attached to the pumping mechanism of FIG. 3C according to a non-limiting embodiment of the disclosure, which is similar to the pumping mechanism shown in FIG. 3B, wherein some of the similar features to the pumping mechanism shown in FIG. 3B are marked with the same reference characters.

In a non-limiting embodiment, the pumping mechanism contains two and only two drive arms (e.g., two of drive arms 40 shown in FIG. 4A or two of drive arms 40 shown in FIG. 4D), and each of the two drive arms have an identical shape. In another embodiment, the pumping mechanism contains four and only four valve arms (e.g., valve arms 17*a*, 17*b*, 18*a*, 18*b* shown in FIGS. 3A and 3C), and each of the four valve arms (e.g., 17*a*, 17*b*, 18*a*, 18*b*) has an identical shape. However, in an alternative embodiment, it is contemplated that the number of drive arms and valve arms could vary.

The surface contact area (see arrow 41) used to generate the force from the pressure against the transducer can be, for example, about one half inch square, which would be over ten times larger than any other system used in the infusion device industry today. This benefits pressure measurement in several important ways. The most important is accuracy. With a large surface area, small changes in pressure result in very large changes in the force read by the strain gage sensor. This increases the gain and sensitivity of the system. As mentioned above, in conventional devices, sophisticated algorithms are applied to use changes in pressures, not actual pressure, to mitigate pressure sensor inaccuracies and reduce the time to trigger an alarm. This software fix is not required by the non-limiting embodiments described herein. Instead, alarm thresholds can be brought close to operating pressure limits because of the stability and accuracy of the system. The accuracy and stability of the system can also be applied to make better use of the software if needed; not as a Band-Aid to fix deficiencies but to enhance the system. Software could be applied to predict pressure trends, reliably, and without introducing the potential for nuisance false alarms.

The present inventors identified that the need for preloading the pressure sensor can be eliminated by mechanically coupling a disposable cassette 20 to a pumping mechanism 10. Exemplary embodiments of a mechanical coupling are disclosed herein. Indeed, a mechanical coupling between the disposable and the pumping mechanism presents several advantages. For example, by mechanical coupling, the sole function of a thermoplastic elastomeric material used as the material of the membrane of the disposable cassette is to seal the fluid path, which keeps stresses on the elastomer very low. Further, relaxation of the elastomer over time will not be a factor and does not contribute to pressure sensing drift or effect accuracy. Further, hysteresis can be effectively eliminated by using very compliant thermoplastic elastomeric materials for the membrane of the disposable. Specific thermoplastic elastomeric materials are not particularly limited, and examples include, for example, polyvinylchloride, high density polyethylene, and polyurethane.

Hysteresis can also be effectively eliminated by coupling the force sensors of the pressure sensing system directly to the pivoting drive arms 13 of the pumping system. Based on the pumping system described in Patent Document 1 and the embodiments described herein, the drive arms 13 pivot with low friction. Further, relatively large forces generated by small changes in pressure make the contribution to errors generated by manufacturing tolerances insignificant.

Referring to FIGS. 4B and 4C, individual force sensors (e.g., strain gauge 42) of the pressure system described herein can be attached to each of two pumping arms 40. The section of the attachment area is optimized to maximize the gain, or output, of the sensor.

Strain "ε" in engineering parlance is a synonym for displacement. More specifically, the length of stretch when loaded divided by the original unloaded length. A strain gauge is a network of resistors, sensitive to displacement arranged in a configuration specific to the application. Different orientations of the resistors detect torsion, plate bending, tension, compression and combinations of these loads. Stress "σ" is the ratio of force applied over the area being subject to load. Stress and strain are related through the geometry of the structure they are attached to. The simpler the structure, the more potential accuracy as these compound deflections often have interactive affects that are difficult to accommodate. An example would be if the sensors were attached to the plate shaped surface area 41 of the pumping drive arm 40 in contact with the disposable cassette, off center loading on the plate, or areas of concentrated stress around the perimeter supporting the plate would introduce errors. This consideration drove an advantageous location for the sensors shown in the drawings. For example, as shown in FIG. 4B, the force sensor (strain gauge 42) is attached to the rectangular cross section beam 43 that is not subject to torsional or off-center loads.

In a non-limiting embodiment, a pair of force sensors (e.g., a pair of strain gauges 42) can be disposed, in concert, to monitor up and downstream pressures continuously and to provide empirically verified gauge pressure accuracies equivalent to or better than a standard industrial pressure gauge or inline digital pressure sensors of +/−5%. This estimate is a worst-case tolerance condition, which includes hysteresis and worst-case manufacturing tolerances.

In addition, in a non-limiting embodiment, the contributions from component manufacturing tolerances to pressure measurement errors can also be significantly reduced by positioning compression return springs 44 on the pumping arms 40 through the contact point 49 of the cam 14. If the springs 44 were positioned above or below the contact point 49 of the cam 14 they would introduce a bending moment on the area of the finger where the force sensor (e.g., strain gauge 42) is mounted. The further the spring 44 is from the contact point 49 on the cam 14, the larger the moment, and the larger the resulting leverage against the force sensor (e.g., strain gage 42). Springs have very loose tolerances. Variations in the spring force against the pumping finger would then introduce errors in the pressure readings. If the springs 44 act directly against the point of contact 49 with the cam 14, the moments and resultant affect from the spring force and variations in force go to zero. Thus, providing compression return springs 44 in this location is advantageous to generate zero moment relative to the beam section 43 on the drive arm 40 so that spring loads do not contribute to the pressure measurement tolerance stack.

The non-limiting embodiments disclosed herein are designed to accommodate manufacturing constraints and reduce cost. Calibration of individual units would add cost but would also improve gauge pressure performance and accuracy if clinically justified. One example of clinical need may be detection of an infiltration. If the injection site misses the vein, fluids are introduced directly into subcutaneous tissue. Due to the nature of drugs being used, this can be extremely harmful, leading to potential amputation, especially in neonates or elderly patients. The dynamic pressure characteristic is very different for an infiltrated injection site and can be differentiated from the full patency of an injection site by sensitive and accurate pressure measurement.

The individual force sensors are not particularly limited. Example sensors include the strain gauge 42 shown in FIGS. 4B and 4C.

The use of strain gauges for the manufacture of pressure sensors is well known. An exemplary strain gauge comprises a flexible backing which supports a metallic foil pattern, and the strain gauge is attached to an object. As the object is deformed, the foil is deformed, causing its electrical resistance to change. The resistance change can be detected/measured, for example, by a pressure system controller and/or a pumping system controller. A pressure system controller or pumping system controller can be defined by a programmed microcomputer including a CPU, RAM and ROM. Alternatively, the sensor could be coupled to a graphic display driver, recorder or storage device.

The force sensor, for example the strain gauge 42, can be fixed to the drive arm 40 by known means, including, for example, a suitable adhesive.

In a non-limiting embodiment, the section of the drive arm beam 43 supporting the strain gages 42 can be engineered, for example, to produce 100 percent strain at a max pressure of 15 psig to maximize the gain of the strain gauges. An added benefit to the strategic location of the strain gauges 42 is that changes and/or failures of critical to function components (including, for example, the motor, gearbox, drive gear, springs, drive arms, bearings and pumping fingers) can be detected by changes in the output of the pressure sensors to either trigger an alarm or signal the controller to halt the infusion and take the device out of service. This is a critical for compliance to safety standards established by the FDA for class 2 medical devices.

The embodiments of the pressure sensing device and system described herein are particularly suitable for use in a pumping system as described in Patent Document 1. Of course, those skilled in the art would understand that the non-limiting embodiments described herein may be configurable for use in alternative systems.

FIGS. 4A-4C, show non-limiting embodiments of the disclosed pressure system device and system, and such embodiments are described above. Modifications could be made, in line with the description herein, as FIGS. 4A-4C merely show preferred embodiments for such a pressuring sensing device and system. For example, when employed in a pumping system of the type described in Patent Document 1, it is contemplated that the sensor could be placed on only one of the drive arms 106, or another alternative is that more than one sensor is placed on each drive arm 106.

In a non-limiting embodiment, the pumping system disclosed herein is configured to monitor a DC output from a pressure sensor (e.g., a strain gauge 42).

In one embodiment, the pumping system contains two and only two drive arms 40, each drive arm 40 includes a strain gauge 42 as the pressure sensor, and the pumping system monitors a DC output from each pressure sensor. In one embodiment, the pumping system can be configured to indicate a failure of the device based on the DC output from either of the strain gauges 42. In another embodiment, the pumping system can be configured to cross reference the output of both strain gauges 42 and the torque requirements of the motor 15 to determine which component within the pumping mechanism failed. In another embodiment, the pumping system can be configured to cross reference the output of both strain gauges 42 from previous pumping cycles.

Reliable AIL Detection

In a non-limiting embodiment, an AIL detection system is disclosed herein that can offer significant improvements in detecting the presence of air and protecting the patient as compared to conventional AIL detection. The non-limiting embodiments disclosed herein also provide a detection system that is more sensitive and reliable as compared to conventional AIL detection by reducing the frequency of false AIL alarms and the alarm fatigue experienced by the medical staff.

Administration set tubing (not shown) is typically bonded to internal fitments on a shell 31 of the disposable cassette 20. This implementation describes an extended distal fitment (see arrow 33) (having the outlet port 24 at its distal end), leading to the AIL sensor 50. The distal fitment can be a molded part of the cassette shell 31. Further, as shown in FIGS. 2A-2C, the distal fitment comprises opposing cut outs 29 for bracketing the AIL sensor 50.

The AIL sensor 50 can be any means for detecting air in the line of fluid flow comprising the distal fitment (see arrow 33) portion of the cassette and the corresponding administration set tubing. In the non-limiting embodiment shown in FIGS. 3A and 3B, the means for detecting AIL is an ultrasonic transducer pair of the type typically used to detect air in IV tubing.

During assembly, the administration tubing (e.g., tubing 64 in FIG. 8D) is bonded to the distal fitment (see arrow 33) of the cassette at positions above (or distal) 32*a* and below (or proximal) 32*b* the contact area with the sensor 50 This serves to isolate the critical area of contact (and provides direct contact between the sensor 50 and the tubing 64) from the effects of distal strain on the tubing. Controlling the location of the tubing also serves to automatically position the tubing as the set is loaded into the case bezel 19, as shown in the non-limiting embodiment of FIGS. 8D-8F, which eliminates the need for manual insertion. This design also fundamentally changes the boundary conditions that define the contact stress profile between the IV tubing and sensor. In addition, the side walls of the tubing will be constrained to minimize material creep and mitigate reductions in sensor coupling associated with cold flow.

In a non-limiting embodiment, the administration tubing is bonded during assembly. For example, the tubing can be solvent bonded, such as with cyclohex. In a non-limiting embodiment, the administration set is received by a customer with distal tubing and proximal tubing already attached. Thus, in one non-limiting embodiment, an administration set 70 shown in FIG. 8D includes a disposable cassette (e.g., the disposable cassette 20 show in FIGS. 2A-2C) having tubing bonded to the inlet port end of the cassette (e.g., the inlet port 23 having a lumen (unlabeled) with the tubing disposed inside the lumen) and tubing bonded to the outlet port end of the cassette (e.g., the outlet port 24 of the distal fitment (see arrow 33) having a lumen (unlabeled) with the tubing disposed inside the lumen). This is because, for example, a typical process of manufacturing an administration set for IV administration would include sterilization and there are numerous configurations and options attached to the set Y sites, filters, check valves, etc. that may be bonded to the IV tubing during assembly as the set is configured.

According to a non-limiting embodiment disclosed herein, the AIL detection is isolated from external forces, which allows for increased sensitivity of the AIL sensor (e.g., an ultrasonic transducer pair), thereby decreasing time to alarm and increasing resolution. This is shown, for example, in the non-limiting embodiment of FIGS. 8D-8F.

According to a non-limiting embodiment disclosed herein, loading the cassette 20 automatically inserts and isolates a viewing window of the fluid path into the AIL sensor. This is shown, for example, in FIG. 8F.

Other Features

Figure 8A:
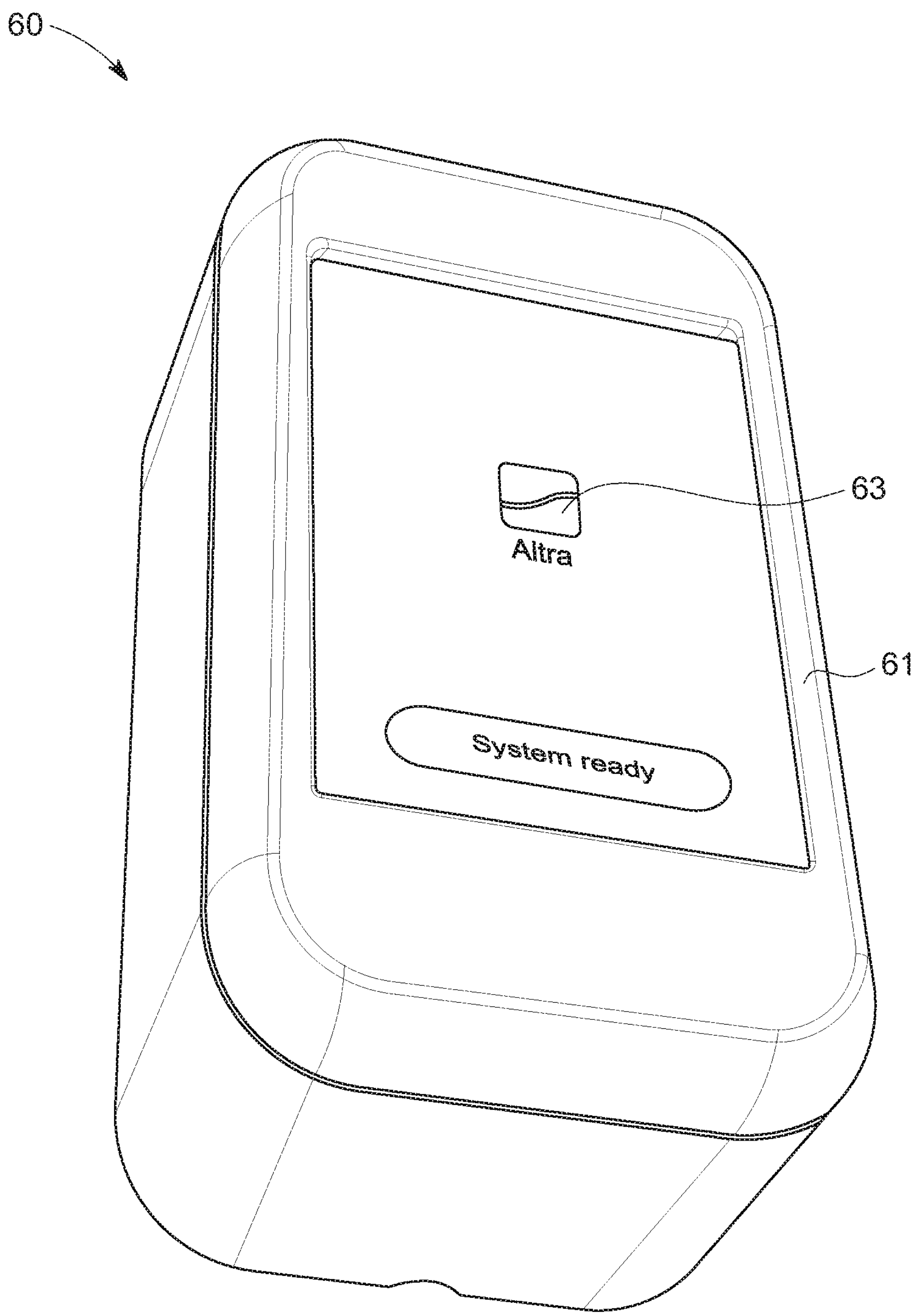
FIGS. 8A-8C show perspective views of a case containing a pumping mechanism according to a non-limiting embodiment of the disclosure.
Figure 8B:
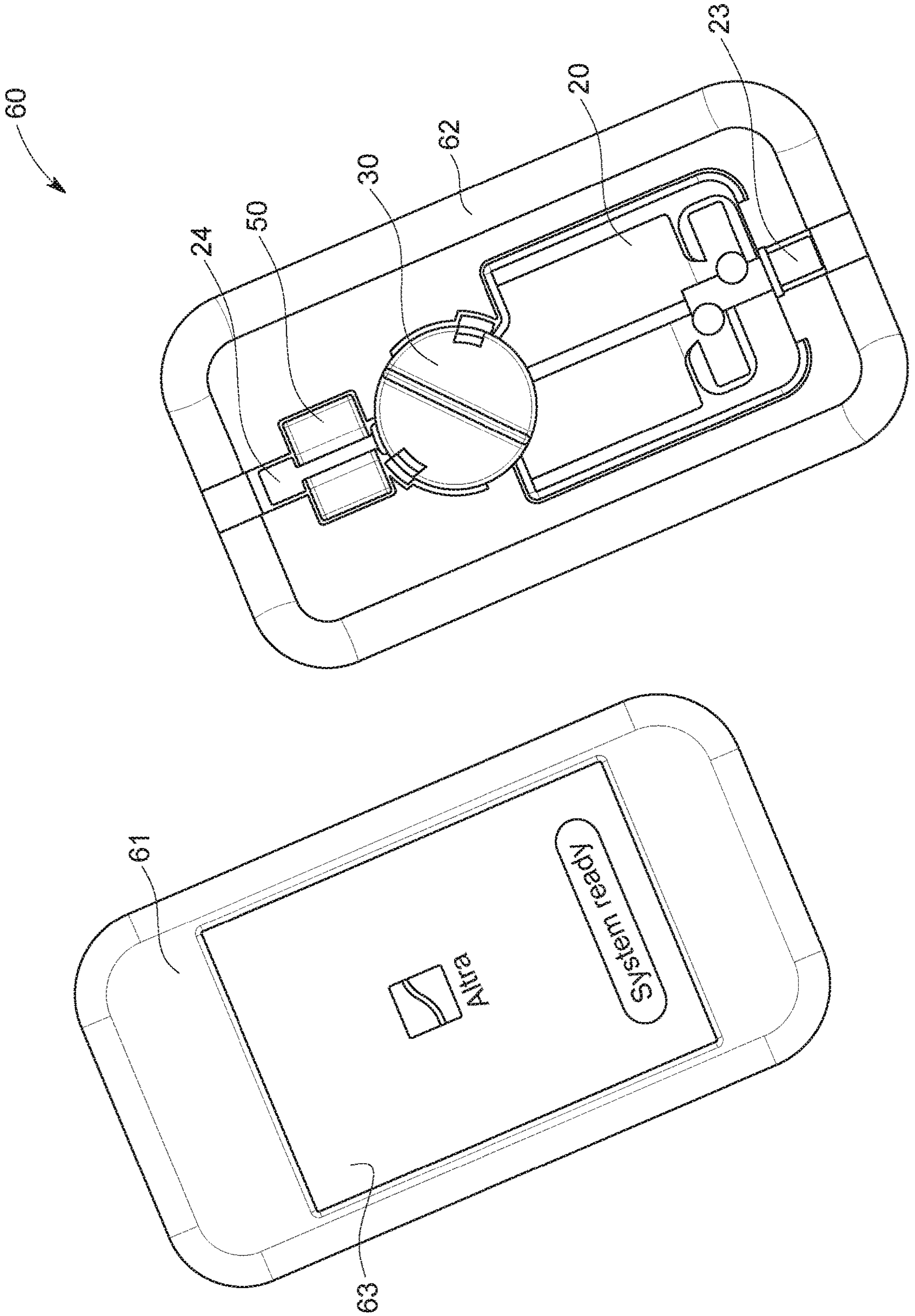
Figure 8C:
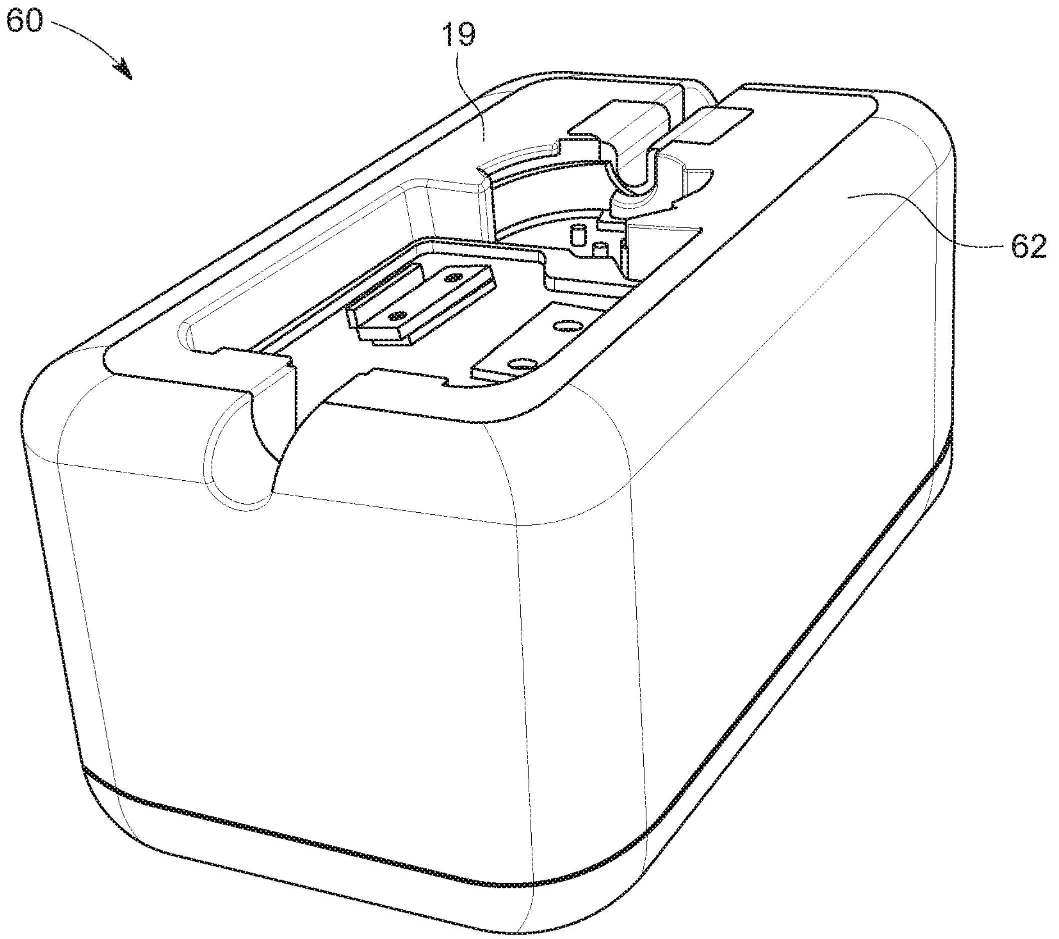
Figure 8D:
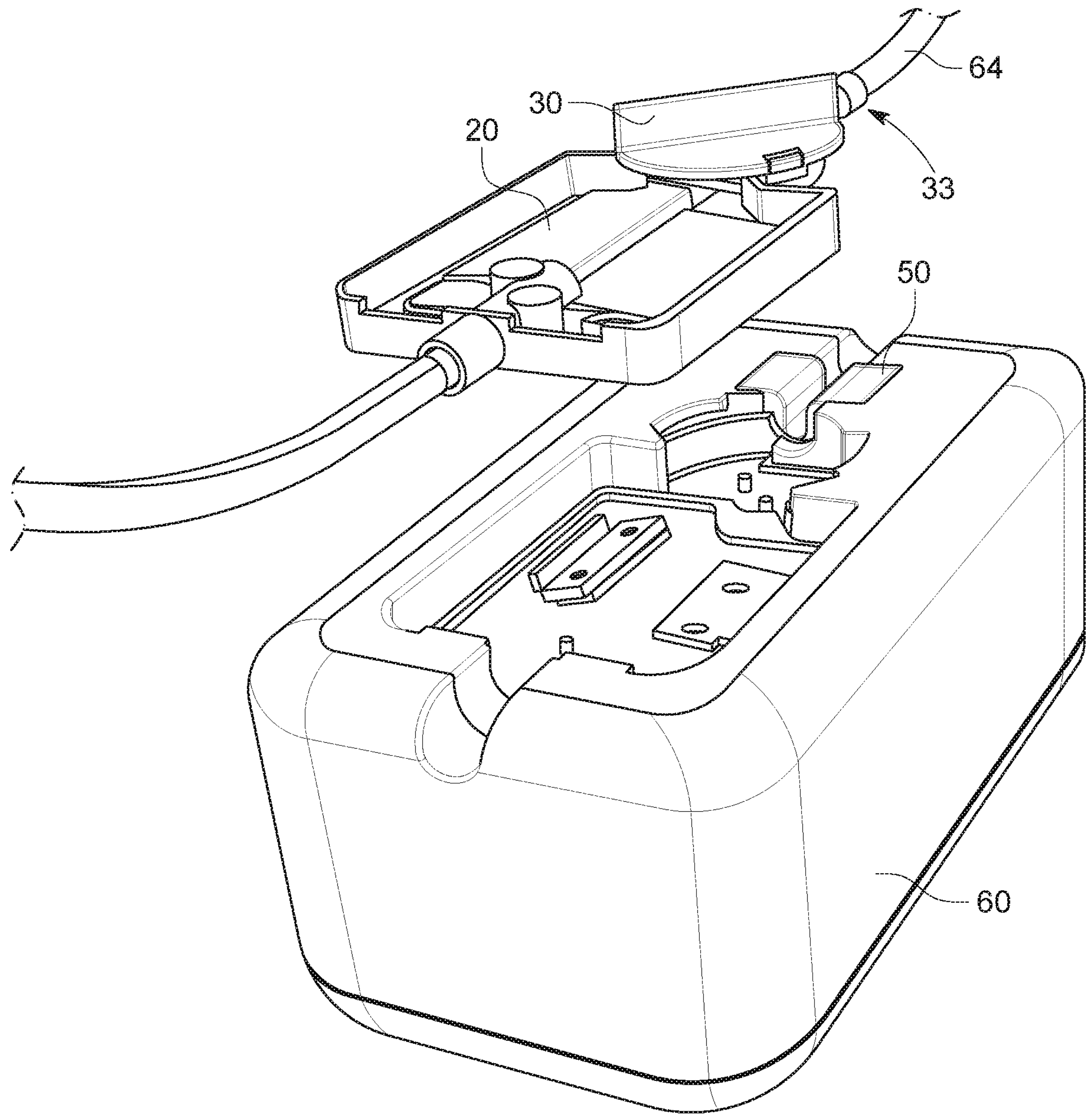
FIGS. 8D-8F show perspective views of the non-limiting embodiment of the case having a non-limiting embodiment of a cassette of the type shown in FIGS. 2A-2F being loaded thereon.
Figure 8E:
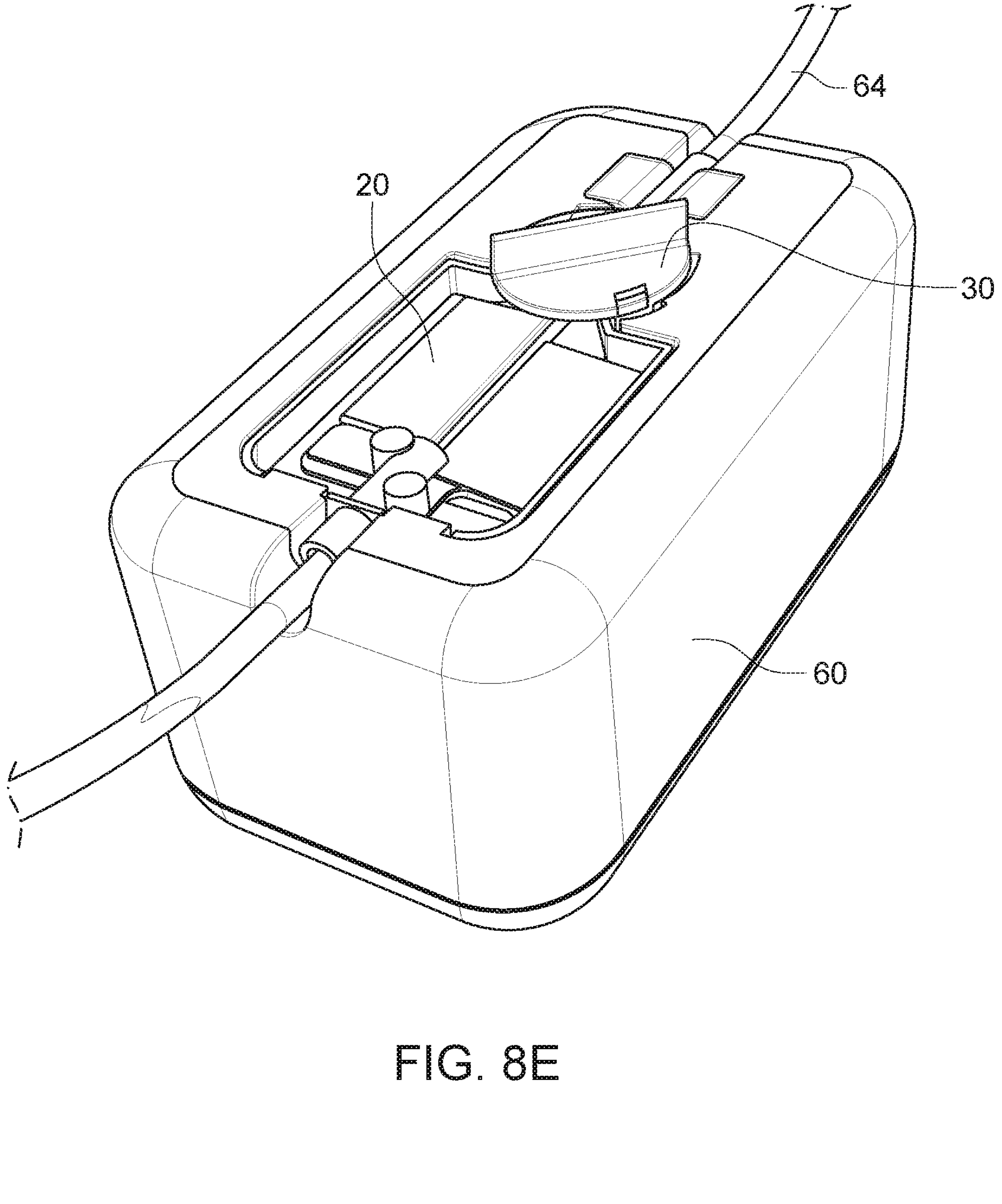
Figure 8F:
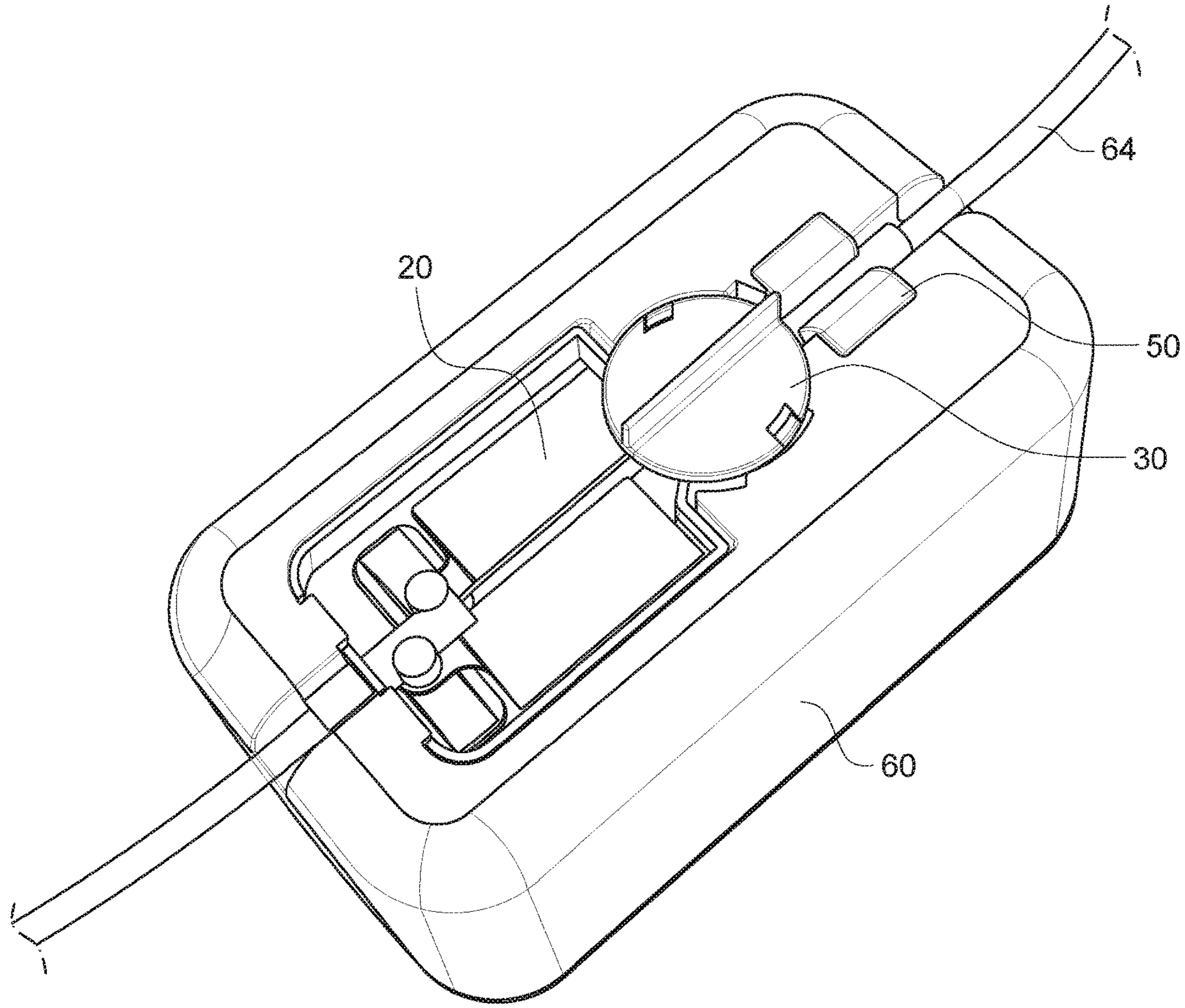

In a non-limiting embodiment shown in FIGS. 8A-8F, the pumping mechanism disclosed herein can be enclosed in a housing or case 60 having, on one external surface 62 of the rectangular housing, means for loading the disposable cassette (see, e.g., FIGS. 8B and 8C, which show, for example, a non-limiting embodiment of bezel 19 having a shape corresponding to a shape of a cassette 20), and on another external surface of the rectangular housing, a graphic display 63 coupled to the above-described microcomputer (see, e.g., FIG. 8B).

In another non-limiting embodiment, the pumping mechanism can include means for wireless communicating with an external microcomputer, wherein exemplary means can include, for example, a combination of hardware and software means for communicating according to the 5G telecommunication standard. Thus, in a non-limiting embodiment, one or more of a pressure sensor (e.g., strain gauges 42), the motor 15 and/or AIL sensor (e.g., ultrasonic transducer pair 50) can be electronically coupled to a microcomputer of the pumping mechanism for the purpose of wirelessly communicating to an external microcomputer any one or more of a pressure determination, an AIL determination, a pressure warning, an AIL warning, or other operating parameter of the pumping mechanism.

In a non-limiting embodiment, the pumping mechanism disclosed herein can be integrally connected to a graphic display 63, such as a display means embodied in the above-described case 60. A non-limiting example is shown in FIG. 8A. In one embodiment, the graphic display 63 can include a resistive touch panel configured to enable the user to operate the touchscreen regardless what comes between the user and the pumping device (e.g., gloves, bodily fluids, dust water, etc.).

In a non-limiting embodiment, the pumping mechanism disclosed herein can have customizable network compatibility to fit customers use requirements from first responders to hospital, home care and military.

In a non-limiting embodiment, the pumping mechanism disclosed herein can be configured for monitoring and control from any device anywhere, including, for example, a central command location.

In a non-limiting embodiment, the pumping mechanism disclosed herein may also include means for NFC (near-field communication) for easy synching with an external NFC capable device.

In a non-limiting embodiment, the pumping mechanism disclosed herein can be powered by a rechargeable battery, such as a lithium ion secondary battery, or alternatively, the pumping mechanism may be coupled to an external power source. In a non-limiting embodiment, the pumping mechanism disclosed herein is powered by a rechargeable battery, and the pumping mechanism is configured to charge the rechargeable battery by inductive charging. For example, in such an inductive charging embodiment, a small charging puck can be placed near a bottom surface (or other surface) of a housing (e.g., case 60) containing the pumping mechanism, wherein the charging puck can be configured to auto align and/or magnetically couple to a surface of the housing.

In a non-limiting embodiment, a system for charging the rechargeable battery operates at 12 volts, which maximizes flexibility and allows the embodiments of the pumping system disclosed herein to be used in the field. In a non-limiting embodiment, the rechargeable battery could be charged with a solar panel, a hand crank, or a car battery. In another embodiment, the rechargeable battery could be charged by coupling the device to a wall outlet.

In a non-limiting embodiment, the pumping mechanism disclosed herein can be enclosed in a housing (e.g., case 60 shown in FIGS. 8A-8F). In one non-limiting embodiment, the case is completely sealed, such that, for example, the case can be IP67 rated (submersible up to one meter for 30 minutes).

In a non-limiting embodiment, the pumping mechanism disclosed herein is controlled by a microcomputer of the type disclosed above, and the microcomputer is programmed with an operating system. In one embodiment, the operating system can be updated by wirelessly communicating with the pumping mechanism. Examples of such wireless communication are discussed above. A benefit of this non-limiting embodiment is that wireless updates allow for safeguards to remain current alongside new drug developments and user interface improvements. Another benefit can be the ability to implement system wide updates immediately without the need to collect and manually update.

While the non-limiting embodiments of the present disclosure have been described in detail using the drawings, the specific configuration is not limited to that of the disclosed embodiments, and any design changes etc. made within the scope of the present disclosure shall be included in the disclosure. Although non-limiting embodiments have been disclosed for illustrative purposes, those skilled in the art will appreciate that various modifications, additions and substitutions are possible with respect to the non-limiting embodiments, without departing from the scope and spirit of the embodiments of the invention as defined in the following claims.

The invention claimed is:

1. An infusing pumping system, comprising:

(A) a disposable cassette comprising:

a body having a sealed top side, an open bottom side, an inlet port, and an outlet port;

a first inlet valve and a second inlet valve in communication with the inlet port;

a first outlet valve and a second outlet valve in communication with the outlet port;

a first pumping chamber disposed within the open bottom side of the body and in communication with the first inlet valve and the first outlet valve;

a second pumping chamber disposed within the open bottom side of the body and in communication with the second inlet port and the second outlet port, the first pumping chamber and the second pumping chamber being positioned on opposing sides of a central axis of the body extending from the inlet port to the outlet port; and a membrane sealing the open bottom side of the body, the membrane comprising a first female feature associated with the first pumping chamber and a second female feature associate with the second pumping chamber; and (B) a pumping mechanism comprising:

a chassis configured for removable attachment to the disposable cassette;

a motor disposed within a length of the chassis and positioned in parallel to the central axis extending between the inlet port and the outlet port of the disposable cassette when the disposable cassette is attached to the pumping system;

a camshaft in mechanical communication with the motor;

a first drive arm hingedly attached to the chassis and positioned parallel to the motor, wherein a bottom portion of the first drive arm is in mechanical communication with the camshaft, and a top portion of the first drive arm has a first male feature configured for coupling to the first female feature of the disposable cassette;

a second drive arm hingedly attached to the chassis and positioned parallel to the motor, wherein a bottom portion of the second drive arm is in mechanical communication with the camshaft, and a top portion of the second drive arm has a second male feature configured for coupling to the second female feature of the disposable cassette, and wherein the first and second drive arms are 180 degrees out of phase with each other during operation of the pumping mechanism; and a plurality of valve arms hingedly attached to the chassis, wherein a lower portion of each of the valve arms is in mechanical communication with the camshaft and an upper portion of each of the valve arms is configured to respectively actuate each of the first inlet valve, the second inlet valve, the first outlet valve, and the second outlet valve of the disposable cassette.

2. The infusion pumping system of claim 1, wherein the first male feature and the second male feature are each located orthogonal to a contacting face of the membrane of the disposable cassette, centered on an axis of rotation of the first and second drive arms, and longitudinal to the central axis.

3. The infusion pumping system of claim 1, wherein the first female feature and the second female feature each comprise a slot in the membrane.

4. The infusion pumping system of claim 1, wherein the first female feature comprises a first slot in the membrane, the second female feature comprises a second slot in the membrane, the first male feature comprises a first blade, and the second male feature comprises a second blade; and wherein the first blade is configured to be releasably fixed to the first slot, and the second blade is configured to be releasably fixed to the second slot.

* * * * *